(12) United States Patent
Torrens Jover et al.

(10) Patent No.: US 8,106,085 B2
(45) Date of Patent: *Jan. 31, 2012

(54) INDOLINE-SUBSTITUTED PYRAZOLINE DERIVATIVES, THEIR PREPARATION AND USE AS MEDICAMENTS

(75) Inventors: Antonio Torrens Jover, Terrasa (ES); Susana Yenes Minguez, Barcelona (ES)

(73) Assignee: Laboratorios Del Dr. Esteve, S.A., Barcelona (ES)

( * ) Notice: Subject to any disclaimer, the term of this patent is extended or adjusted under 35 U.S.C. 154(b) by 721 days.

This patent is subject to a terminal disclaimer.

(21) Appl. No.: 11/995,766

(22) PCT Filed: Jul. 17, 2006

(86) PCT No.: PCT/EP2006/007011
§ 371 (c)(1),
(2), (4) Date: Sep. 22, 2008

(87) PCT Pub. No.: WO2007/009721
PCT Pub. Date: Jan. 25, 2007

(65) Prior Publication Data
US 2009/0131497 A1    May 21, 2009

Related U.S. Application Data

(60) Provisional application No. 60/705,432, filed on Aug. 5, 2005.

(30) Foreign Application Priority Data

Jul. 15, 2005   (EP) .................................. 05384029

(51) Int. Cl.
*A61K 31/4155*  (2006.01)
*C07D 231/06*   (2006.01)
(52) U.S. Cl. ..................................... 514/403; 548/364.4
(58) Field of Classification Search ............... 548/364.4; 514/403
See application file for complete search history.

(56) References Cited

U.S. PATENT DOCUMENTS

| | | | |
|---|---|---|---|
| 5,017,596 A | 5/1991 | Colombo et al. |
| 5,624,941 A | 4/1997 | Barth et al. |
| 5,849,931 A | 12/1998 | Frigola-Constansa et al. |
| 6,118,009 A | 9/2000 | Torrens-Jover et al. |
| 6,187,930 B1 | 2/2001 | Torrens-Jover et al. |
| 6,410,582 B1 | 6/2002 | Merce-Vidal et al. |
| 6,509,367 B1 | 1/2003 | Martin et al. |
| 6,610,737 B1 | 8/2003 | Garzon et al. |
| 6,956,033 B2 | 10/2005 | Ogawa et al. |
| 7,829,581 B2 | 11/2010 | Torrens Jover et al. |
| 2002/0058816 A1 | 5/2002 | Kordik et al. |
| 2002/0156104 A1 | 10/2002 | Adams et al. |
| 2003/0022925 A1 | 1/2003 | Merce-Vidal et al. |
| 2003/0153569 A1 | 8/2003 | Adams et al. |
| 2004/0092535 A1 | 5/2004 | Barsanti et al. |
| 2005/0137251 A1 | 6/2005 | Garzon et al. |
| 2005/0171179 A1 | 8/2005 | Lange et al. |
| 2005/0222138 A1 | 10/2005 | Ohhata et al. |
| 2005/0282798 A1 | 12/2005 | Lazzari et al. |
| 2006/0020010 A1 | 1/2006 | Altisen et al. |
| 2006/0052315 A1 | 3/2006 | Leung et al. |
| 2006/0106014 A1 | 5/2006 | Boddupalli et al. |
| 2006/0128673 A1 | 6/2006 | Firnges et al. |
| 2006/0172019 A1 | 8/2006 | Ralston et al. |
| 2006/0189658 A1 | 8/2006 | Altisen et al. |
| 2006/0194843 A1 | 8/2006 | Berdini et al. |

FOREIGN PATENT DOCUMENTS

| | | |
|---|---|---|
| GB | 1209326 | 10/1970 |
| JP | 02117605 A | 10/1988 |
| WO | 8805046 A2 | 7/1988 |
| WO | 8806583 | 9/1988 |
| WO | 9203421 | 3/1992 |
| WO | 0076503 A1 | 12/2000 |
| WO | 01/70700 A | 9/2001 |
| WO | 02080909 A1 | 10/2002 |
| WO | 2004060882 A1 | 7/2004 |
| WO | 2004078261 A1 | 9/2004 |
| WO | 2005/077911 A | 8/2005 |
| WO | 2006077414 A1 | 7/2006 |
| WO | 2006077419 A1 | 7/2006 |
| WO | 2006077425 A1 | 7/2006 |
| WO | 2006077428 A1 | 7/2006 |

OTHER PUBLICATIONS

Bryn et al, Solid State Chemistry of Drugs, 2nd edition, 1999, SSCI, Inc, Chapter 10, Polymorphs, p. 232-247.*
NIMH—Eating Disorders, accessed on Mar. 7, 2011 from http://www.nimh.nih.gov/health/publications/eating-disorders/completeindex.shtml.*

(Continued)

Primary Examiner — Andrew D Kosar
Assistant Examiner — Karen Cheng
(74) Attorney, Agent, or Firm — Banner & Witcoff, Ltd.

(57) ABSTRACT

The present invention relates to indoline-substituted pyrazoline compounds of formula (I), methods for their preparation, medicaments comprising these compounds as well as their use for the preparation of a medicament for the treatment of humans and animals.

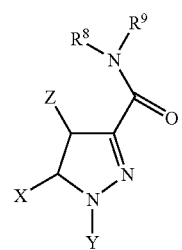

(I)

22 Claims, No Drawings

OTHER PUBLICATIONS

Tonstad, S., "Rimonabant: A cannabinoid receptor blocker for the treatment of metabolic and cardiovascular risk factors," 2006, Nutrition, Metabolism and Cardiovascular Diseases, 16, p. 156-162.*
Vippagunta et al, "Crystalline solids," 2001, Advanced Drug Delivery Reviews, 48, p. 3-26.*
Chan et al.; "N-substituted Pyrazoline-type Insecticides"; ACS Symposium Series, No. 800, p. 144-155 (2002); Chem. Abstr. XP002335857.
Meier et al.; "Insecticidal Dihydropyrazoles with Reduced Lipophilicity"; ACS Symposium Series, No. 504, p. 313-326 (1992); Chem. Abstr. XP002335858.
Meyer et al.; "1,5-Diaryl-2, 3-pyrrolidinediones—Phenylhydrazine Derivatives"; Journal of Organic Chemistry, vol. 22, p. 1565-1567 (1957); Chem. Abstr. XP002335859.
International Search Report mailed Jul. 29, 2005 in International Application No. PCT/EP20058/001659.
Tamura, Kenji et al.; "One-Pot Synthesis of Trifluoroacetimidoyl Halides"; Journal of Organic Chemistry (1993), vol. 58, p. 32-38.
Hollister, Leo E.; "Health Aspects of Cannabis"; Pharmacological Reviews, vol. 38, No. 1, p. 1-20 (1986).
Murphy, L. et al.; Consroe and Sandyk; "Potential Role of Cannabinoids for Therapy of Neurological Disorders"; p. 459-524, CRC Press (1992).
Slavinska, V. et al.; "New Way for the Preparation of 4-Phenyl-2-Oxobutyric Acid Ethyl Ester"; Synthetic Communications, 26(11), p. 2229-2233 (1996).
Dujardin, G. et al.; "A Straightforward Route to E Aryl-a-oxobutenoic Esters by One-step Acid-catalysed Crotonisation of Pyruvates"; Synlett, No. 1, p. 147-149 (2001).
Pascual, Alfons; "Synthese des 5-[)Acetylhydrazono)-(4-chlorphenyl)-methyl]thiophen-2yl-esters der Trifluomethansulfonsaure"; J. Prakt. Chem. 341, No. 7, p. 695-700 (1999).
Lin, Shrong-Shi et al.; "Regioselective Friedel-Crafts Acylation with Unsymmetrically Substituted Furandicarboxylic Acid Anhydride and Furan Acid Chloride: Syntheses of 4-Substituted 3-Arylcarbonyl-2-Phenylfuran and 3-Substituted 4-Arylcarbonyl-2-Phenylfuran"; Heterocycles, vol. 55, No. 2, p. 265-277 (2001).
Rao, P.D. et al.; "Rational Syntheses of Porphyrins Bearing up to Four Different Meso Substituents"; J. Org. Chem., 65, p. 7323-7344 (2000).
Pearson, D.E. et al.; "Friedel-Crafts Acylations with Little or No Catalyst"; Synthesis, No. 10: October, p. 533-542 (1972).
Ross, Ruth A. et al.; "Agonist-Inverse agonist characterization at CB1 and CB2 cannabinoid receptors of L-759633, L759656 and AM630"; British Journal of Pharmacology 126, p. 665-672 (1999).
Howlett, A.C. et al.; "International Union of Pharmacology XXVII. Classification of Cannabinoid Receptors"; Pharmacological Reviews 54, p. 161-202 (2002).
Compton, David R. et al.; "In-Vivo Characterization of a Specific Cannabinoid Receptor Antagonist (SR141716A): Inhibition of Δ9—Tetrahydrocannabinol-Induced Responses and Apparent Agonist Activity"; The Journal of Pharmacology and Experimental Therapeutics, vol. 277, No. 2, p. 588-594 (1996).
Woolfe, G. et al.; "The Evaluation of the Analgesic Action of Pethidine Hydrochloride (Demerol)"; The Journal Of Pharmacology and Experimental Therapeutics, vol. 80, p. 300-307 (1944).
Desmedt, L.K.C. et al.; "Anticonvulsive Properties of Cinnarizine and Flunarizine in Rats and Mice"; Arzneim Forsch (Drug Res.) 25, No. 9, p. 1408-1413 (1975).
Colombo, G. et al.; "Appetite Suppression and Weight Loss after teh cannabinoid Antagonist SR 141716"; Life Sciences, vol. 63, No. 8, p. PL 113-117 (1998).
Alpermann, H.G. et al.; "Pharmacological Effects of Hoe 249: A New Potential Antidepressant", Drug Development Research, 25, p. 267-282 (1992).
Seth, R. et al.; "Chemistry and Pharmacology of Cannabis"; Progress in Drug Research, vol. 36, p. 71-115 (1991).
Muccioli, G.G. et al.; "CB1 and CB2 cannabinoid receptor antagonists and inverse agonists for obesity, metabolic syndrome and smoking cessation indications"; Expert Opinion on Therapeutic Patents, vol. 16, No. 10, p. 1405-1423 (2006).
Lange, J.H.M. et al.; "3,4-diarylpyrozolines as cannabinoid CB SUB 1 receptor antagonists with lower lipophilicity"; Bioorganic & Medicinal Chemistry Letters, vol. 15, No. 21, p. 4794-4798 (2005).
Thomas, B.F. et al.; "Long-chain amide analogs of the cannabinoid CB1 receptor antagonist N-(piperidinyl)-5-(4- chlorophenyl)-1-(2,4-dichlorophenyl)-4-methyl-1H-pyrazole-3-carboxamide"; Bioorganic & Medicinal Chemistry, vol. 13, No. 18, p. 5463-5474 (2005).
Dyck, et al. "Potent Imidazole and Triazole CB1 Receptor Antagonists Related to SR141716", Bioorganic & Medicinal Chemistry Letters, 2004, pp. 1151-1154, vol. 14, Oxford, GB.
Wiley et al.; (2005) British Journal of Pharmacology; vol. 145, pp. 293-300.
Di Marzo et al.; (May 2005) Nature Neuroscience; vol. 8, No. 5, pp. 585-589.

* cited by examiner

INDOLINE-SUBSTITUTED PYRAZOLINE DERIVATIVES, THEIR PREPARATION AND USE AS MEDICAMENTS

CROSS-REFERENCE TO RELATED APPLICATIONS

This application is a U.S. National Stage application under 35 U.S.C. §371 of International Application No. PCT/EP2006/007011 (published as WO 2007/009721 A2), filed Jul. 17, 2006, which claims priority to the following applications: EP Application No. 05384029.4, filed Jul. 15, 2005 and U.S. Provisional Application Ser. No. 60/705,432, filed Aug. 5, 2005. Benefit of the filing date of each of these prior applications is hereby claimed. Each of these prior applications is hereby incorporated by reference in its entirety.

The present invention relates to indoline-substituted pyrazoline compounds, methods for their preparation, medicaments comprising these compounds as well as their use for the preparation of a medicament for the treatment of humans and animals.

Cannabinoids are compounds, which are derived from the cannabis sativa plant which is commonly known as marijuana. The most active chemical compound of the naturally occurring cannabinoids is tetrahydrocannabinol (THC), particularly $\Delta^9$-THC.

These naturally occurring cannabinoids as well as their synthetic analogues promote their physiological effects via binding to specific G-coupled receptors, the so-called cannabinoid-receptors.

At present, two distinct types of receptors that bind both the naturally occurring and synthetic cannabinoids have been identified and cloned. These receptors, which are designated $CB_1$ and $CB_2$ are involved in a variety of physiological or pathophysiological processes in humans and animals, e.g. processes related to the central nervous system, immune system, cardiovascular system, endocrinous system, respiratory system, the gastrointestinal tract or to reproduction, as described for example, in Hollister, Pharm. Rev. 38, 1986, 1-20; Reny and Singha, Prog. Drug. Res., 36, 71-114, 1991; Consroe and Sandyk, in Marijuana/Cannabinoids, Neurobiology and Neurophysiology, 459, Murphy L. and Barthe A. Eds., CRC Press, 1992.

Therefore, compounds, which have a high binding affinity for these cannabinoid receptors and which are suitable for modulating these receptors are useful in the prevention and/or treatment of cannabinoid-receptor related disorders.

In particular, the $CB_1$-Receptor is involved in many different food-intake related disorders such as bulimia or obesity, including obesity associated with type II diabetes (non-insulin-dependent diabetes) and thus, compounds suitable for regulating this receptor may be used in the prophylaxis and/or treatment of these disorders.

Thus, it was an object of the present invention to provide novel compounds for use as active substances in medicaments. In particular, these active substances should be suitable for the modulation of Cannabinoid receptors, more particularly for the modulation of Cannabinoid 1 ($CB_1$) receptors.

Said object was achieved by providing the cycloalkane-substituted pyrazoline compounds of general formula I given below, their stereoisomers, corresponding salts and corresponding solvates thereof.

It has been found that these compounds have a high affinity for cannabinoid receptors, particularly for the $CB_1$-receptor, and that they act as modulators e.g. antagonists, inverse agonists or agonists on these receptors. They are therefore suitable for the prophylaxis and/or treatment of various disorders related to the central nervous system, the immune system, the cardiovascular system, the endocrinous system, the respiratory system, the gastrointestinal tract or reproduction in humans and/or animals, preferably humans including infants, children and grown-ups.

Thus, in one of its aspects the present invention relates to substituted Indoline-substituted pyrazoline compounds of general formula I,

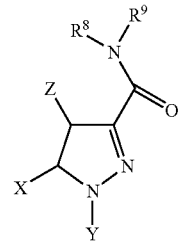

I wherein

Z is selected from $C_{1-4}$-Alkyl, substituted or unsubstituted, branched or linear, saturated or unsaturated;

X and Y independently represent phenyl, thienyl, naphtyl or pyridyl which groups may be substituted with 1, 2 or 3 substituents W, which can be the same or different, selected from the group
branched or linear $C_{1-3}$-alkyl or branched or linear $C_{1-3}$-alkoxy, phenyl, hydroxy, chloro, bromo, fluoro, iodo, SH, trifluoromethyl, $CHF_2$, $CH_2F$, $OCHF_2$, trifluoromethylthio, trifluoromethoxy, methylsulfonyl, carboxyl, trifluoromethylsulfonyl, cyano, carbamoyl, sulfamoyl and acetyl; O—P, with P denominating a prodrug group consisting of aryl, $C_{8-20}$-alkyl, heteroaryl, C(O)-aryl, C(O)heteroaryl, C(O)—$C_{1-20}$-alkyl;

$R^8$ representing a hydrogen atom or a branched or linear $C_{1-3}$-alkyl group, while $R^9$ is representing

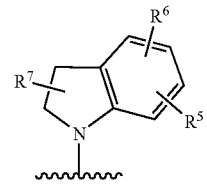

with $R^5$, $R^6$ and $R^7$ being independently from one another selected from H, F, Cl, Br, I, OH, SH, $C_{1-4}$alkyl, $C_{1-4}$alkoxy, $CF_3$, $CHF_2$, $CH_2F$, $OCF_3$, a keto-group, $NO_2$ or $NH_2$;

or $R^8$ and $R^9$ together with the connecting Nitrogen atom are representing

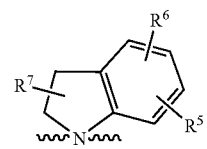

with $R^5$, $R^6$ and $R^7$ being independently from one another selected from H, F, Cl, Br, I, OH, SH, $C_{1-4}$alkyl, $C_{1-4}$alkoxy, $CF_3$, $CHF_2$, $CH_2F$, $OCF_3$, a keto-group, $NO_2$ or $NH_2$;

optionally in the form of its racemate, pure stereoisomers, especially enantiomers or diastereomers or in the form of mixtures of stereoisomers, especially enantiomers or diastereomers, in any suitable ratio;

in the form shown or in form of the acid or base or in form of a salt, especially a physiologically acceptable salt, or in form of a solvate, especially a hydrate or in form of a corresponding N-oxide thereof.

In the context of this invention, alkyl radical or group is understood as meaning saturated and unsaturated, linear or branched hydrocarbons, which can be unsubstituted or mono- or polysubstituted. Thus unsaturated alkyl is understood to encompass alkenyl and alkinyl groups, like e.g. —CH═CH—CH$_3$ or —C≡C—CH$_3$, while saturated alkyl encompasses e.g. —CH$_3$ and —CH$_2$—CH$_3$. In these radicals, $C_{1-2}$-alkyl represents C1- or C2-alkyl, $C_{1-3}$-alkyl represents C1-, C2- or C3-alkyl, $C_{1-2}$-alkyl represents C1-, C2-, C3- or C4-alkyl, $C_{1-5}$-alkyl represents C1-, C2-, C3-, C4-, or C5-alkyl, $C_{1-6}$-alkyl represents C1-, C2-, C3-, C4-, C5- or C6-alkyl, $C_{1-7}$-alkyl represents C1-, C2-, C3-, C4-, C5-, C6- or C7-alkyl, $C_{1-8}$-alkyl represents C1-, C2-, C3-, C4-, C5-C6-, C7- or C8-alkyl, $C_{1-10}$-alkyl represents C1-, C2-, C3-, C4-, C5-, C6-, C7-, C8-, C9- or C10-alkyl and $C_{1-18}$-alkyl represents C1-, C2-, C3-, C4-, C5-, C6-, C7-, C8-, C9-, C10-, C111-, C12-, C13-, C14-, C15-, C16-, C17- or C18-alkyl. The alkyl radicals are preferably methyl, ethyl, vinyl (ethenyl), propyl, allyl (2-propenyl), 1-propinyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, if substituted also $CHF_2$, $CF_3$ or $CH_2OH$ etc.

In the context of this invention cycloalkyl radical or group is understood as meaning saturated and unsaturated (but not aromatic) cyclic hydrocarbons (without a heteroatom in the ring), which can be unsubstituted or mono- or polysubstituted. Furthermore, $C_{3-4}$-cycloalkyl represents C3- or C4-cycloalkyl, $C_{3-5}$-cycloalkyl represents C3-, C4- or C5-cycloalkyl, $C_{3-6}$-cycloalkyl represents C3-, C4-, C5- or C6-cycloalkyl, $C_{3-7}$-cycloalkyl represents C3-, C4-, C5-, C6- or C7-cycloalkyl, $C_{3-8}$-cycloalkyl represents C3, C4-, C5-, C6-, C7- or C8-cycloalkyl, $C_{4-5}$-cycloalkyl represents C4 or C5-cycloalkyl, $C_{4-6}$-cycloalkyl represents C4, C5- or C6-cycloalkyl, $C_{4-7}$-cycloalkyl represents C4-, C5-, C6- or C7-cycloalkyl, $C_{4-8}$-cycloalkyl represents C4-, C5-, C6-C7- or C8-cycloalkyl $C_{5-6}$-cycloalkyl represents C5- or C6-cycloalkyl and $C_{5-7}$-cycloalkyl represents C5-, C6- or C7-cycloalkyl. However, mono- or polyunsaturated, preferably monounsaturated, cycloalkyls also in particular fall under the term cycloalkyl as long as the cycloalkyl is not an aromatic system. The alkyl and cycloalkyl radicals are preferably methyl, ethyl, vinyl (ethenyl), propyl, allyl (2-propenyl), 1-propinyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, cyclopropyl, 2-methylcyclopropyl, cyclopropylmethyl, cyclobutyl, cyclopentyl, cyclopentylmethyl, cyclohexyl, cycloheptyl, cyclooctyl, and also adamantly.

In connection with alkyl or aliphatic group—unless defined otherwise—the term substituted in the context of this invention is understood as meaning replacement of at least one hydrogen radical by F, Cl, Br, I, $NH_2$, SH or OH, "polysubstituted" radicals being understood as meaning that the replacement takes effect both on different and on the same atoms several times with the same or different substituents, for example three times on the same C atom, as in the case of $CF_3$, or at different places, as in the case of e.g. —CH(OH)—CH═CH—CHCl$_2$.

The term $(CH_2)_{3-6}$ is to be understood as meaning —CH$_2$—CH$_2$—CH$_2$—, —CH$_2$—CH$_2$—CH$_2$—CH$_2$—, —CH$_2$—CH$_2$—CH$_2$—CH$_2$—CH$_2$— and —CH$_2$—CH$_2$—CH$_2$—CH$_2$—CH$_2$—CH$_2$—, $(CH_2)_{1-4}$ is to be understood as meaning —CH$_2$—, —CH$_2$—CH$_2$—, —CH$_2$—CH$_2$—CH$_2$— and —CH$_2$—CH$_2$—CH$_2$—CH$_2$—, $(CH_2)_{4-5}$ is to be understood as meaning —CH$_2$—CH$_2$—CH$_2$—CH$_2$ and —CH$_2$—CH$_2$—CH$_2$—CH$_2$—CH$_2$—, etc.

An aryl radical or group is understood as meaning ring systems with at least one aromatic ring but without heteroatoms even in only one of the rings. Examples are phenyl, naphthyl, fluoranthenyl, fluorenyl, tetralinyl or indanyl, in particular 9H-fluorenyl or anthracenyl radicals, which can be unsubstituted or monosubstituted or polysubstituted.

In the context of this invention alkyl-aryl is understood as meaning an aryl group (see above) being connected to another atom through an alkyl-group (see above) (preferably a $C_{1-4}$-alkyl), whereas the alkyl is always saturated and linear or branched always refers to the alkyl. Examples include a benzyl-group A heterocycyl radical or group is understood as meaning heterocylic ring systems, saturated or unsaturated ring which contains one or more heteroatoms from the group consisting of nitrogen, oxygen and/or sulfur in the ring and can also be mono- or polysubstituted. Examples which may be mentioned from the group of heterocyclyls are furan, benzofuran, thiophene, benzothiophene, pyrrole, pyridine, pyrimidine, pyrazine, quinoline, isoquinoline, phthalazine, benzo-1,2,5-thiadiazole, benzothiazole, indole, benzotriazole, benzodioxane, benzodioxane, carbazole and quinazoline.

In the context of this invention alkyl-heterocylyl is understood as meaning a heterocylyl group (see above) being connected to another atom through an alkyl group (see above) (preferably a $C_{1-4}$-alkyl), whereas the alkyl is always saturated and linear or branched always refers to the alkyl.

In connection with aryl or alkyl-aryl, cycloalkyl or alkyl-cycloalkyl, heterocyclyl or alkyl-heterocyclyl, substituted is understood—unless defined otherwise—as meaning substitution of the ring-system of the aryl or alkyl-aryl, cycloalkyl or alkyl-cycloalkyl; heterocycyl or alkyl-heterocycyl by OH, SH, ═O, halogen (F, Cl, Br, I), CN, $NO_2$, COOH; $NR_xR_y$, with $R_x$ and $R_y$ independently being either H or a saturated or unsaturated, linear or branched, substituted or unsubstituted $C_{1-6}$-alkyl; a saturated or unsaturated, linear or branched, substituted or unsubstituted $C_{1-6}$-alkyl; a saturated or unsaturated, linear or branched, substituted or unsubstituted —O—$C_{1-6}$alkyl (alkoxy); a saturated or unsaturated, linear or branched, substituted or unsubstituted —S—$C_{1-6}$-alkyl; a saturated or unsaturated, linear or branched, substituted or unsubstituted —C(O)—$C_{1-6}$-alkyl-group; a saturated or unsaturated, linear or branched, substituted or unsubstituted —C(O)—O—$C_{1-6}$-alkyl-group; a substituted or unsubstituted aryl or alkyl-aryl; a substituted or unsubstituted cycloalkyl or alkyl-cycloalkyl; a substituted or unsubstituted heterocycyl or alkyl-heterocyclyl.

The term "salt" is to be understood as meaning any form of the active compound used according to the invention in which it assumes an ionic form or is charged and is coupled with a counter-ion (a cation or anion) or is in solution. By this are also to be understood complexes of the active compound with other molecules and ions, in particular complexes which are complexed via ionic interactions.

The term "physiologically acceptable salt" means in the context of this invention any salt that is physiologically tolerated (most of the time meaning not being toxic—especially not caused by the counter-ion) if used appropriately for a treatment especially if used on or applied to humans and/or mammals.

These physiologically acceptable salts can be formed with cations or bases and in the context of this invention is understood as meaning salts of at least one of the compounds used according to the invention—usually a (deprotonated) acid—as an anion with at least one, preferably inorganic, cation which is physiologically tolerated—especially if used on humans and/or mammals. The salts of the alkali metals and alkaline earth metals are particularly preferred, and also those with NH4, but in particular (mono)- or (di)sodium, (mono)- or (di)potassium, magnesium or calcium salts.

These physiologically acceptable salts can also be formed with anions or adds in the context of this invention is understood as meaning salts of at least one of the compounds used according to the invention—usually protonated, for example on the nitrogen—as the cation with at least one anion which are physiologically tolerated—especially if used on humans and/or mammals. By this is understood in particular, in the context of this invention, the salt formed with a physiologically tolerated acid, that is to say salts of the particular active compound with inorganic or organic adds which are physiologically tolerated—especially if used on humans and/or mammals. Examples of physiologically tolerated salts of particular acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid or citric acid.

The compounds of the invention may be in crystalline form or either as free compounds or as solvates and it is intended that those forms are within the scope of the present invention. Methods of solvation are generally known within the art. Suitable solvates are pharmaceutically acceptable solvates. The term "solvate" according to this invention is to be understood as meaning any form of the active compound according to the invention in which this compound has attached to it via non-covalent binding another molecule (most likely a polar solvent) especially including hydrates and alcoholates, e.g. methanolate.

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon or $^{15}N$-enriched nitrogen are within the scope of this invention.

The compounds of formula (I) or their salts or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I) or, or of its salts, solvates or prodrugs.

In a preferred embodiment of the invention the Indoline-substituted pyrazoline compounds according to the invention are of general formulas Ia or Ib

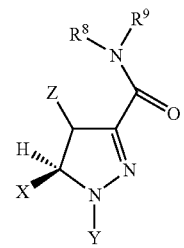

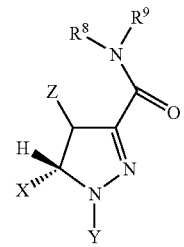

wherein

Z is selected from $C_{1-4}$-Alkyl, substituted or unsubstituted, branched or linear, saturated or unsaturated;

X and Y independently represent phenyl, thienyl, naphtyl or pyridyl which groups may be substituted with 1, 2 or 3 substituents W, which can be the same or different, from the group:
branched or linear $C_{1-3}$-alkyl or branched or linear $C_{1-3}$-alkoxy, phenyl, hydroxy, chloro, bromo, fluoro, iodo, SH, trifluoromethyl, $CHF_2$, $CH_2F$, $OCHF_2$, trifluoromethylthio, trifluoromethoxy, methylsulfonyl, carboxyl, trifluoromethylsulfonyl, cyano, carbamoyl, sulfamoyl and acetyl; O—P, with P denominating a prodrug group consisting of aryl, $C_{8-20}$-alkyl, heteroaryl, C(O)-aryl, C(O)-heteroaryl, C(O)—$C_{1-20}$-alkyl;

$R^8$ representing a hydrogen atom or a branched or linear $C_{1-3}$-alkyl group, while $R^9$ is representing

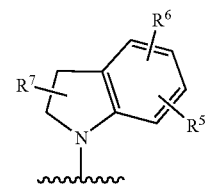

with $R^5$, $R^6$ and $R^7$ being independently from one another selected from H, F, Cl, Br, I, OH, SH, $C_{1-4}$alkyl, $C_{1-4}$alkoxy, $CF_3$, $CHF_2$, $CH_2F$, $OCF_3$, a keto-group, $NO_2$ or $NH_2$;

or $R^8$ and $R^9$ together with the connecting Nitrogen atom are representing

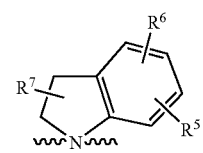

with $R^5$, $R^6$ and $R^7$ being independently from one another selected from H, F, Cl, Br, I, OH, SH, $C_{1-4}$alkyl, $C_{1-4}$alkoxy, $CF_3$, $CHF_2$, $CH_2F$, $OCF_3$, a keto-group, $NO_2$ or $NH_2$;

optionally in the form shown or in form of the acid or base or in form of a salt, especially a physiologically acceptable salt, or in form of a solvate, especially a hydrate or in form of a corresponding N-oxide thereof.

As there are 2 stereogenic centers in the molecules the compounds of general formulas Ia and Ib may actually show the following relative configuration:

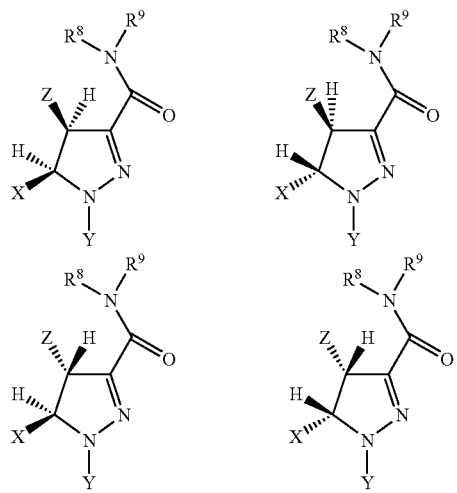

In a preferred embodiment of the invention the Indoline-substituted pyrazoline compounds according to the invention are of general formula II,

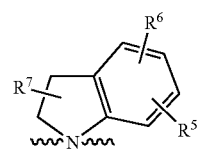

II wherein

Z' is selected from $C_{1-4}$-Alkyl, substituted or unsubstituted, branched or linear, saturated or unsaturated; preferably is either $CH_3$ or $C_2H_5$;

$R^{11}$, $R^{12}$, $R^{13}$ and $R^{14}$ independently of one another represent:

H; branched or linear $C_{1-3}$-alkyl or branched or linear $C_{1-3}$-alkoxy, phenyl, hydroxy, chloro, bromo, fluoro, iodo, SH, trifluoromethyl, $CHF_2$, $CH_2F$, $OCHF_2$, trifluoromethylthio, trifluoromethoxy, methylsulfonyl, carboxyl, trifluoromethylsulfonyl, cyano, carbamoyl, sulfamoyl and acetyl; O—P, with P denominating a prodrug group consisting of aryl, $C_{8-20}$-alkyl, heteroaryl, C(O)-aryl, C(O)-heteroaryl, C(O)—$C_{1-20}$-alkyl;

$R^{18}$ representing a hydrogen atom or a branched or linear $C_{1-3}$-alkyl group, while $R^{19}$ is representing

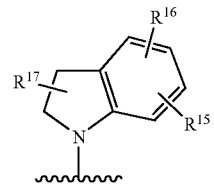

with $R^{15}$, $R^{16}$ and $R^{17}$ are independently from one another selected from, H, F, Cl, Br, I, OH, SH, $C_{1-4}$alkyl, $C_{1-4}$alkoxy, $CF_3$, $CHF_2$, $CH_2F$, $OCF_3$, a keto-group, $NO_2$ or $NH_2$;

or $R^{18}$ and $R^{19}$ together with the connecting Nitrogen atom are representing

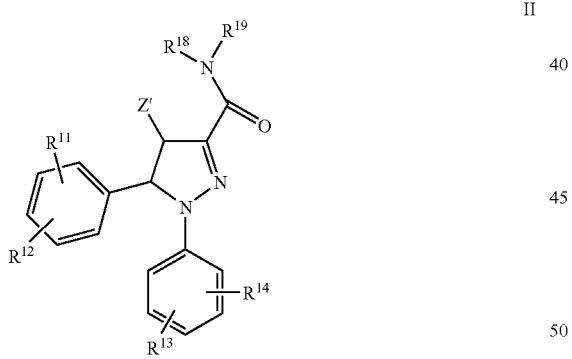

with $R^{15}$, $R^{16}$ and $R^{17}$ are independently from one another selected from, H, F, Cl, Br, I, OH, SH, $C_{1-4}$alkyl, $C_{1-4}$alkoxy, $CF_3$, $CHF_2$, $CH_2F$, $OCF_3$, a keto-group, $NO_2$ or $NH_2$;

optionally in the form of its racemate, pure stereoisomers, especially enantiomers or diastereomers or in the form of mixtures of stereoisomers, especially enantiomers or diastereomers, in any suitable ratio;

in the form shown or in form of the acid or base or in form of a salt, especially a physiologically acceptable salt, or in form of a solvate, especially a hydrate or in form of a corresponding N-oxide thereof.

In a preferred embodiment of the invention the Indoline-substituted pyrazoline compounds according to the invention are of general formulas IIa or IIb

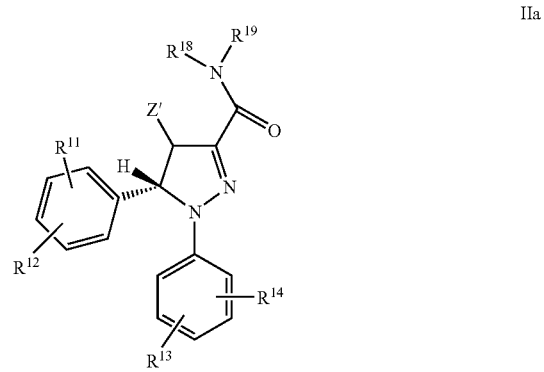

IIa

-continued

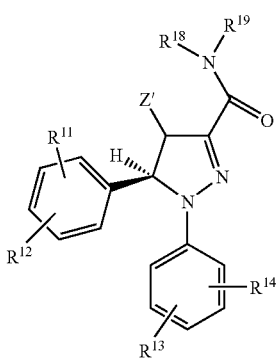

IIb wherein
Z' is selected from $C_{1-4}$-Alkyl, substituted or unsubstituted, branched or linear, saturated or unsaturated; preferably is either $CH_3$ or $C_2H_5$;
$R^{11}$, $R^{12}$, $R^{13}$ and $R^{14}$ independently of one another represent:
H; branched or linear $C_{1-3}$-alkyl or branched or linear $C_{1-3}$-alkoxy, phenyl, hydroxy, chloro, bromo, fluoro, iodo, SH, trifluoromethyl, trifluoromethylthio, trifluoromethoxy, $CHF_2$, $CH_2F$, $OCHF_2$, methylsulfonyl, carboxyl, trifluoromethylsulfonyl, cyano, carbamoyl, sulfamoyl and acetyl; O—P, with P denominating a prodrug group consisting of aryl, $C_{8-20}$-alkyl, heteroaryl, C(O)-aryl, C(O)-heteroaryl, C(O)—$C_{1-20}$-(alkyl);
$R^{18}$ representing a hydrogen atom or a branched or linear $C_{1-3}$-alkyl group, while $R^{19}$ is representing

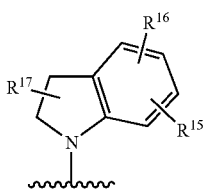

with $R^{15}$, $R^{16}$ and $R^{17}$ are independently from one another selected from, H, F, Cl, Br, I, OH, SH, $C_{1-4}$alkyl, $C_{1-4}$alkoxy, $CF_3$, $CHF_2$, $CH_2F$, $OCF_3$, a keto-group, $NO_2$ or $NH_2$;
or
$R^{18}$ and $R^{19}$ together with the connecting Nitrogen atom are representing

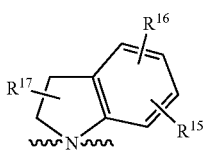

with $R^{15}$, $R^{16}$ and $R^{17}$ are independently from one another selected from, H, F, Cl, Br, I, OH, SH, $C_{1-4}$alkyl, $C_{1-4}$alkoxy, $CF_3$, $CHF_2$, $CH_2F$, $OCF_3$, a keto-group, $NO_2$ or $NH_2$;
optionally in the form shown or in form of the acid or base or in form of a salt, especially a physiologically acceptable salt, or in form of a solvate, especially a hydrate or in form of a corresponding N-oxide thereof.

In a preferred embodiment of the invention the Indoline-substituted pyrazoline compounds according to the invention of general formulas II, IIa or IIb are characterized in that
$R^{11}$, $R^{12}$, $R^{13}$ and $R^{14}$ independently of one another represent H, $CH_3$, $C_2H_5$, $C_3H_7$, $OCH_3$, $OC_2H_5$, OH, SH, F, Cl, Br, I $CF_3$, $CHF_2$, $CH_2F$, $OCF_3$, $OCHF_2$; preferably $R^{11}$, $R^{12}$, $R^{13}$ and $R^{14}$ independently of one another represent H, OH, $OCH_3$, F, Cl, Br, I, $CF_3$, $CHF_2$ or $OCF_3$.

In a preferred embodiment of the invention the Indoline-substituted pyrazoline compounds according to the invention of general formulas II, IIa or IIb are characterized in that $R^{18}$ represents H.

In a preferred embodiment of the invention the Indoline-substituted pyrazoline compounds according to the invention of general formulas II, IIa or IIb are characterized in that $R^{15}$, $R^{16}$ and $R^{17}$ are independently from one another selected from, H, F, Cl, Br, I, OH, $CH_3$, $C_2H_5$, $OCH_3$, $OCF_3$, or $CF_3$.

In a preferred embodiment of the invention the Indoline-substituted pyrazoline compounds according to the invention are of general formula III,

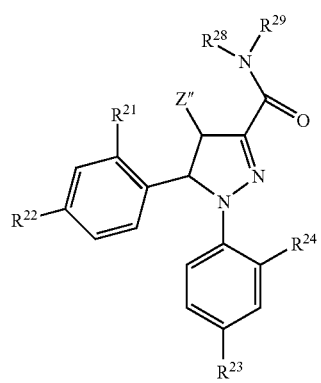

III wherein
Z'' is selected from $CH_3$ or $C_2H_5$;
$R^{21}$, $R^{22}$, $R^{23}$ and $R^{24}$ independently of one another represent:
H; branched or linear $C_{1-3}$-alkyl or branched or linear $C_{1-3}$-alkoxy, phenyl, hydroxy, chloro, bromo, fluoro, iodo, SH, trifluoromethyl, trifluoromethylthio, trifluoromethoxy, methylsulfonyl, carboxyl, trifluoromethylsulfonyl, cyano, carbamoyl, sulfamoyl and acetyl; O—P, with P denominating a prodrug group consisting of aryl, $C_{8-20}$-alkyl, heteroaryl, C(O)-aryl, C(O)-heteroaryl, C(O)—$C_{1-20}$-alkyl;
$R^{28}$ representing a hydrogen atom or a branched or linear $C_{1-3}$-alkyl group, while $R^{29}$ is representing

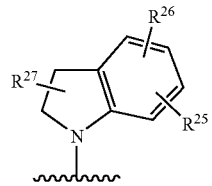

with $R^{25}$, $R^{26}$ and $R^{27}$ are independently from one another selected from, H, F, Cl, Br, I, OH, SH, $C_{1-4}$alkyl, $C_{1-4}$alkoxy, $CF_3$, $CHF_2$, $CH_2F$, $OCF_3$, a keto-group, $NO_2$ or $NH_2$;

or $R^{28}$ and $R^{29}$ together with the connecting Nitrogen atom are representing

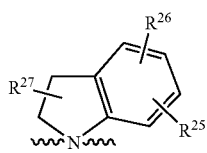

with $R^{25}$, $R^{26}$ and $R^{27}$ are independently from one another selected from, H, F, Cl, Br, I, OH, SH, $C_{1-4}$alkyl, $C_{1-4}$alkoxy, $CF_3$, $CHF_2$, $CH_2F$, $OCF_3$, a keto-group, $NO_2$ or $NH_2$;

optionally in the form of its racemate, pure stereoisomers, especially enantiomers or diastereomers or in the form of mixtures of stereoisomers, especially enantiomers or diastereomers, in any suitable ratio;

in the form shown or in form of the acid or base or in form of a salt, especially a physiologically acceptable salt, or in form of a solvate, especially a hydrate or in form of a corresponding N-oxide thereof.

In a preferred embodiment of the invention the Indoline-substituted pyrazoline compounds according to the invention are of general formulas IIIa or IIIb,

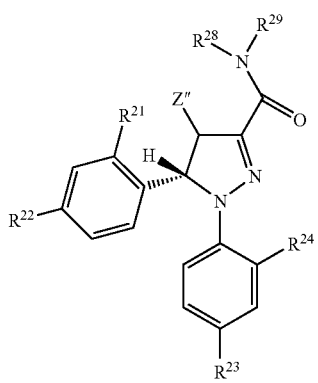

IIIa

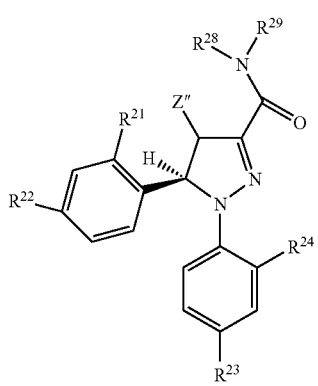

IIIb wherein

Z" is selected from $CH_3$ or $C_2H_5$;

$R^{21}$, $R^{22}$, $R^{23}$ and $R^{24}$ independently of one another represent:

H; branched or linear $C_{1-3}$-alkyl or branched or linear $C_{1-3}$-alkoxy, phenyl, hydroxy, chloro, bromo, fluoro, iodo, SH, trifluoromethyl, trifluoromethylthio, trifluoromethoxy, methylsulfonyl, carboxyl, trifluoromethylsulfonyl, cyano, carbamoyl, sulfamoyl and acetyl; O—P, with P denominating a prodrug group consisting of aryl, $C_{8-20}$-alkyl, heteroaryl, C(O)-aryl, C(O)-heteroaryl, C(O)—$C_{1-20}$-alkyl;

$R^{28}$ representing a hydrogen atom or a branched or linear $C_{1-3}$-alkyl group, while $R^{29}$ is representing

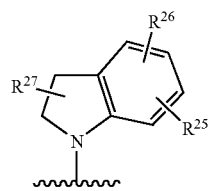

with o being 1 or 2; and with $R^{25}$, $R^{26}$ and $R^{27}$ are independently from one another selected from, H, F, Cl, Br, I, OH, SH, $C_{1-4}$alkyl, $C_{1-4}$alkoxy, $CF_3$, $CHF_2$, $CH_2F$, $OCF_3$, a keto-group, $NO_2$ or $NH_2$;

or $R^{28}$ and $R^{29}$ together with the connecting Nitrogen atom are representing

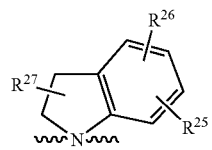

with o being 1 or 2; and with $R^{25}$, $R^{26}$ and $R^{27}$ are independently from one another selected from, H, F, Cl, Br, I, OH, SH, $C_{1-4}$alkyl, $C_{1-4}$alkoxy, $CF_3$, $CHF_2$, $CH_2F$, $OCF_3$, a keto-group, $NO_2$ or $NH_2$;

optionally in the form shown or in form of the acid or base or in form of a salt, especially a physiologically acceptable salt, or in form of a solvate, especially a hydrate or in form of a corresponding N-oxide thereof.

In a preferred embodiment of the invention the Indoline-substituted pyrazoline compounds according to the invention of general formulas III, IIIa or IIIb are characterized in that $R^{21}$ represents; O—P, with P denominating a prodrug group consisting of aryl, $C_{8-20}$-alkyl, heteroaryl, C(O)-aryl, C(O)-heteroaryl, C(O)—$C_{1-20}$-alkyl, while $R^{22}$, $R^{23}$ and $R^{24}$ independently of one another represent H, $CH_3$, $C_2H_5$, $C_3H_7$, $OCH_3$, $OC_2H_5$, OH, SH, F, Cl, Br, I $CF_3$, $CHF_2$, $CH_2F$, $OCF_3$, $OCHF_2$;

preferably $R^{21}$ represents; O—P, with P denominating a prodrug group consisting of aryl, $C_{8-20}$-alkyl, heteroaryl, C(O)-aryl, C(O)-heteroaryl, C(O)—$C_{1-20}$-alkyl, while $R^{22}$, $R^{23}$ and $R^{24}$ independently of one another represent H, OH, $OCH_3$, F, Cl, Br, I, $CF_3$, $CHF_2$ or $OCF_3$;

most preferably $R^{21}$ represents; O—P, with P denominating a prodrug group consisting of aryl, $C_{8-20}$-alkyl, heteroaryl, C(O)-aryl, C(O)-heteroaryl, C(O)—$C_{1-20}$-alkyl, while $R^{22}$, $R^{23}$ and $R^{24}$ independently of one another represent OH, $OCH_3$, F, Cl, Br, I or $OCF_3$.

In a preferred embodiment of the invention the Indoline-substituted pyrazoline compounds according to the invention of general formulas III, IIIa or IIIb are characterized in that
$R^{21}$, $R^{22}$, $R^{23}$ and $R^{24}$ independently of one another represent H, $CH_3$, $C_2H_5$, $C_3H_7$, $OCH_3$, $OC_2H_5$, OH, SH, F, Cl, Br, I $CF_3$, $CHF_2$, $CH_2F$, $OCF_3$, $OCHF_2$; preferably
$R^{21}$, $R^{22}$, $R^{23}$ and $R^{24}$ independently of one another represent H, OH, $OCH_3$, F, Cl, Br, I, $CF_3$, $CHF_2$ or $OCF_3$; most preferably
$R^{21}$ represents H, while $R^{22}$, $R^{23}$ and $R^{24}$ independently of one another represent OH, $OCH_3$, F, Cl, Br, I or $OCF_3$.

In a preferred embodiment of the invention the Indoline-substituted pyrazoline compounds according to the invention of general formulas III, IIIa or IIIb are characterized in that $R^{28}$ represents H.

In a preferred embodiment of the invention the Indoline-substituted pyrazoline compounds according to the invention of general formulas III, IIIa or IIIb are characterized in that
$R^{25}$, $R^{26}$ and $R^{27}$ are independently from one another selected from, H, F, Cl, Br, I, OH, $CH_3$, $C_2H_5$, $OCH_3$, $OCF_3$, or $CF_3$.

In a preferred embodiment of the invention the Indoline-substituted pyrazoline compounds according to the invention are of general formulas IV, IVa or IVb,

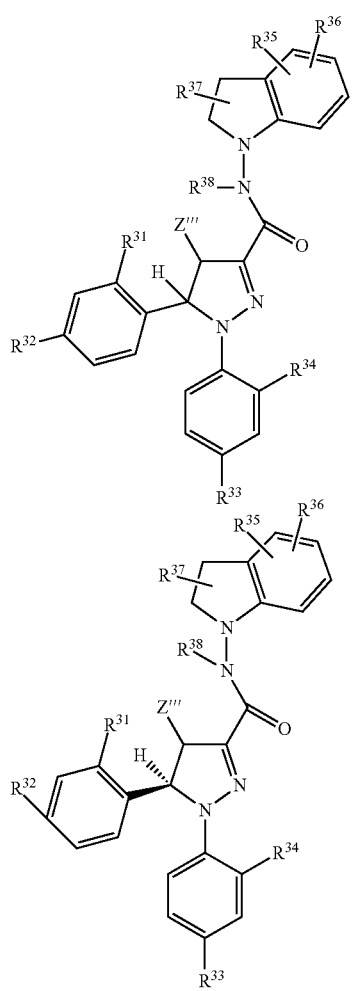

IV

IVa

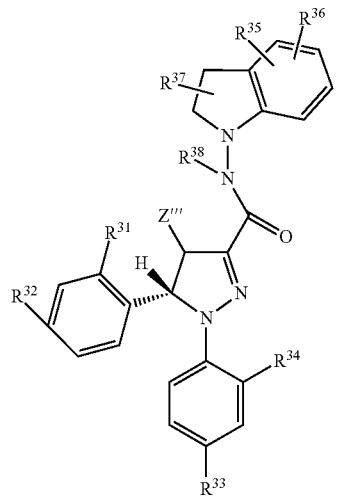

IVb wherein
Z''' is selected from $CH_3$ or $C_2H_5$;
$R^{31}$, $R^{32}$, $R^{33}$ and $R^{34}$ independently of one another represent:
H; branched or linear $C_{1-3}$-alkyl or branched or linear $C_{1-3}$-alkoxy, phenyl, hydroxy, chloro, bromo, fluoro, iodo, SH, trifluoromethyl, trifluoromethylthio, trifluoromethoxy, methylsulfonyl, carboxyl, trifluoromethylsulfonyl, cyano, carbamoyl, sulfamoyl and acetyl; O—P, with P denominating a prodrug group consisting of aryl, $C_{8-20}$-alkyl, heteroaryl, C(O)-aryl, C(O)-heteroaryl, C(O)—$C_{1-20}$-alkyl;
$R^{35}$, $R^{36}$ and $R^{37}$ are independently from one another selected from, H, F, Cl, Br, I, OH, SH, $C_{1-4}$alkyl, $C_{1-4}$alkoxy, $CF_3$, $CHF_2$, $CH_2F$, $OCF_3$, a keto-group, $NO_2$ or $NH_2$;
$R^{38}$ representing a hydrogen atom or a branched or linear $C_{1-3}$-alkyl group;
optionally in the form shown or in form of the acid or base or in form of a salt, especially a physiologically acceptable salt, or in form of a solvate, especially a hydrate or in form of a corresponding N-oxide thereof.

In a preferred embodiment of the invention the Indoline-substituted pyrazoline compounds according to the invention are of general formulas IVc, IVd or IVe, IVc

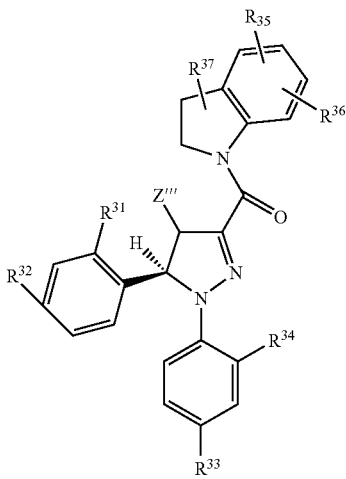

wherein
Z''' is selected from $CH_3$ or $C_2H_5$;
$R^{31}$, $R^{32}$, $R^{33}$ and $R^{34}$ independently of one another represent:
H; branched or linear $C_{1-3}$-alkyl or branched or linear $C_{1-3}$-alkoxy, phenyl, hydroxy, chloro, bromo, fluoro, iodo, SH, trifluoromethyl, trifluoromethylthio, trifluoromethoxy, methylsulfonyl, carboxyl, trifluoromethylsulfonyl, cyano, carbamoyl, sulfamoyl and acetyl; O—P, with P denominating a prodrug group consisting of aryl, $C_{8-20}$-alkyl, heteroaryl, C(O)-aryl, C(O)-heteroaryl, C(O)—$C_{1-20}$-alkyl;
p is 1 or 2;
$R^{35}$, $R^{36}$ and $R^{37}$ are independently from one another selected from, H, F, Cl, Br, I, OH, SH, $C_{1-4}$alkyl, $C_{1-4}$alkoxy, $CF_3$, $CHF_2$, $CH_2F$, $OCF_3$, a keto-group, $NO_2$ or $NH_2$;
optionally in the form shown or in form of the acid or base or in form of a salt, especially a physiologically acceptable salt, or in form of a solvate, especially a hydrate or in form of a corresponding N-oxide thereof.

In a preferred embodiment of the invention the Indoline-substituted pyrazoline compounds according to the invention of general formulas IV, IVa, IVb, IVc, IVd, IVe are characterized in that
$R^{31}$ represents; O—P, with P denominating a prodrug group consisting of aryl, $C_{8-20}$-alkyl, heteroaryl, C(O)-aryl, C(O)-heteroaryl, C(O)—$C_{1-20}$-alkyl, while
$R^{32}$, $R^{33}$ and $R^{34}$ independently of one another represent H, $CH_3$, $C_2H_5$, $C_3H_7$, $OCH_3$, $OC_2H_5$, OH, SH, F, Cl, Br, I $CF_3$, $CHF_2$, $CH_2F$, $OCF_3$, $OCHF_2$;
preferably
$R^{31}$ represents; O—P, with P denominating a prodrug group consisting of aryl, $C_{8-20}$-alkyl, heteroaryl, C(O)-aryl, C(O)-heteroaryl, C(O)—$C_{1-20}$-alkyl, while
$R^{32}$, $R^{33}$ and $R^{34}$ independently of one another represent H, OH, $OCH_3$, F, Cl, Br, I, $CF_3$, $CHF_2$ or $OCF_3$;
most preferably
$R^{31}$ represents; O—P, with P denominating a prodrug group consisting of aryl, $C_{8-20}$-alkyl, heteroaryl, C(O)-aryl, C(O)-heteroaryl, C(O)—$C_{1-20}$-alkyl, while
$R^{32}$, $R^{33}$ and $R^{34}$ independently of one another represent OH, $OCH_3$, F, Cl, Br, I or $OCF_3$.

In a preferred embodiment of the invention the Indoline-substituted pyrazoline compounds according to the invention of general formulas IV, IVa, IVb, IVc, IVd, IVe are characterized in that
$R^{31}$, $R^{32}$, $R^{33}$ and $R^{34}$ independently of one another represent H, $CH_3$, $C_2H_5$, $C_3H_7$, $OCH_3$, $OC_2H_5$, OH, SH, F, Cl, Br, I $CF_3$, $CHF_2$, $CH_2F$, $OCF_3$, $OCHF_2$; preferably
$R^{31}$, $R^{32}$, $R^{33}$ and $R^{34}$ independently of one another represent H, OH, $OCH_3$, F, Cl, Br, I, $CF_3$, $CHF_2$ or $OCF_3$;
most preferably
$R^{31}$ represents H, while $R^{32}$, $R^{33}$ and $R^{34}$ independently of one another represent OH, $OCH_3$, F, Cl, Br, I or $OCF_3$.

In a preferred embodiment of the invention the Indoline-substituted pyrazoline compounds according to the invention of general formulas IV, IVa, IVb, IVc, IVd, IVe are characterized in that
$R^{38}$ represents H.

In a preferred embodiment of the invention the Indoline-substituted pyrazoline compounds according to the invention of general formulas IV, IVa, IVb, IVc, IVd, IVe are characterized in that
$R^{35}$, $R^{36}$ and $R^{37}$ are independently from one another selected from, H, F, Cl, Br, I, OH, $CH_3$, $C_2H_5$, $OCH_3$, $OCF_3$, or $CF_3$, preferably $R^{35}$, $R^{36}$ and $R^{37}$ are H.

In a preferred embodiment of the invention the Indoline-substituted pyrazoline compounds according to the invention of general formulas IV, IVa, IVb, IVc, IVd, IVe are selected from the group consisting of:
cis-5-(4-chlorophenyl)-1-(2,4-dichlorophenyl)-N-(indolin-1-yl)-4-methyl-4,5-dihydro-1H-pyrazole-3-carboxamide
trans-5-(4-chlorophenyl)-1-(2,4-dichlorophenyl)-N-(indolin-1-yl)-4-methyl-4,5-dihydro-1H-pyrazole-3-carboxamide
(4R,5R)-5-(4-chlorophenyl)-1-(2,4-dichlorophenyl)-N-(indolin-1-yl)-4-methyl-4,5-dihydro-1H-pyrazole-3-carboxamide
(4S,5S)-5-(4-chlorophenyl)-1-(2,4-dichlorophenyl)-N-(indolin-1-yl)-4-methyl-4,5-dihydro-1H-pyrazole-3-carboxamide
cis-5-(4-chlorophenyl)-1-(2,4-dichlorophenyl)-4-methyl-N-(2-methylindolin-1-yl)-4,5-dihydro-1H-pyrazole-3-carboxamide
cis-5-(4-bromophenyl)-1-(2,4-dichlorophenyl)-N-(indolin-1-yl)-4-methyl-4,5-dihydro-1H-pyrazole-3-carboxamide
trans-5-(4-bromophenyl)-1-(2,4-dichlorophenyl)-N-(indolin-1-yl)-4-methyl-4,5-dihydro-1H-pyrazole-3-carboxamide
cis-1-(2,4-dichlorophenyl)-5-(4-fluorophenyl)-N-(indolin-1-yl)-4-methyl-4,5-dihydro-1H-pyrazole-3-carboxamide
trans-1-(2,4-dichlorophenyl)-5-(4-fluorophenyl)-N-(indolin-1-yl)-4-methyl-4,5-dihydro-1H-pyrazole-3-carboxamide cis-1-(2,4-dichlorophenyl)-N-(indolin-1-yl)-5-(4-iodophenyl)-4-methyl-4,5-dihydro-1H-pyrazole-3-carboxamide
trans-1-(2,4-dichlorophenyl)-N-(indolin-1-yl)-5-(4-iodophenyl)-4-methyl-4,5-dihydro-1H-pyrazole-3-carboxamide
cis-1-(2,4-dichlorophenyl)-N-(indolin-1-yl)-5-(4-methoxyphenyl)-4-methyl-4,5-dihydro-1H-pyrazole-3-carboxamide
trans-1-(2,4-dichlorophenyl)-N-(indolin-1-yl)-5-(4-methoxyphenyl)-4-methyl-4,5-dihydro-1H-pyrazole-3-carboxamide
cis-1-(2,4-dichlorophenyl)-5-(4-hydroxyphenyl)-N-(indolin-1-yl)-4-methyl-4,5-dihydro-1H-pyrazole-3-carboxamide
trans-1-(2,4-dichlorophenyl)-5-(4-hydroxyphenyl)-N-(indolin-1-yl)-4-methyl-4,5-dihydro-1H-pyrazole-3-carboxamide
cis-5-(5-chlorothiophen-2-yl)-1-(2,4-dichlorophenyl)-N-(indolin-1-yl)-4-methyl-4,5-dihydro-1H-pyrazole-3-carboxamide
trans-5-(5-chlorothiophen-2-yl)-1-(2,4-dichlorophenyl)-N-(indolin-1-yl)-4-methyl-4,5-dihydro-1H-pyrazole-3-carboxamide
cis-5-(5-bromothiophen-2-yl)-1-(2,4-dichlorophenyl)-N-(indolin-1-yl)-4-methyl-4,5-dihydro-1H-pyrazole-3-carboxamide
trans-5-(5-bromothiophen-2-yl)-1-(2,4-dichlorophenyl)-N-(indolin-1-yl)-4-methyl-4,5-dihydro-1H-pyrazole-3-carboxamide
cis-5-(4-chlorophenyl)-1-(2,4-dichlorophenyl)-4-ethyl-N-(indolin-1-yl)-4,5-dihydro-1H-pyrazole-3-carboxamide
trans-5-(4-chlorophenyl)-1-(2,4-dichlorophenyl)-4-ethyl-N-(indolin-1-yl)-4,5-dihydro-1H-pyrazole-3-carboxamide
cis-5-(4-bromophenyl)-1-(2,4-dichlorophenyl)-4-ethyl-N-(indolin-1-yl)-4,5-dihydro-1H-pyrazole-3-carboxamide
trans-5-(4-bromophenyl)-1-(2,4-dichlorophenyl)-4-ethyl-N-(indolin-1-yl)-4,5-dihydro-1H-pyrazole-3-carboxamide
optionally in the form of its racemate, pure stereoisomers, especially enantiomers or diastereomers or in the form of mixtures of stereoisomers, especially enantiomers or diastereomers, in any suitable ratio; optionally in the form of a corresponding N-oxide, a corresponding salt or a corresponding solvate.

In another aspect the present invention also provides a process for the preparation of Indoline-substituted pyrazoline compounds of general formula I given above, wherein at least one benzaldehyde compound of general formula V

(V)

wherein X has the meaning described above, is reacted with a pyruvate compound of general formula (VI)

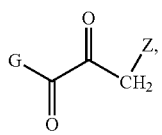

(VI)

wherein Z has the meaning as described above and G represents an OR group with R being H or a branched or unbranched $C_{1-6}$ alkyl radical or G represents an O⁻K⁺ group with K being a cation,
to yield a compound of general formula (VII)

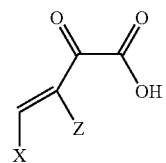

(VII)

wherein Z and X have the meaning given above, which is optionally isolated and/or optionally purified, and which is reacted with an optionally substituted phenyl hydrazine of general formula (VIII)

(VIII)

or a corresponding salt thereof, wherein Y has the meaning described above, under inert atmosphere, to yield a compound of general formula (IX)

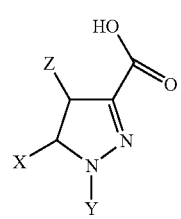

(IX)

wherein X, Z and Y have the meaning as given above, which is optionally isolated and/or optionally purified, and optionally transferred under inert atmosphere to a compound of general formula (XI) via the reaction with an activating agent

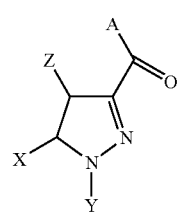

(XI)

wherein the substituents X, Z and Y have the meaning given above and A represents a leaving group, said compound being optionally isolated and/or optionally purified, and at least one compound of general formula (XI) is reacted with a compound of general formula XII or XIIa

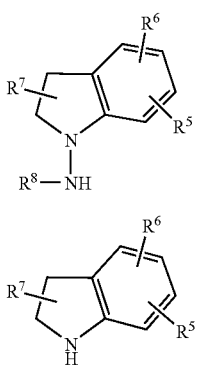

wherein n, $R^5$, $R^6$, $R^7$ and $R^8$ are defined as described above; under inert atmosphere to yield a substituted pyrazoline compound of general formula I, which is optionally isolated and/or optionally purified.

The inventive process is also illustrated in scheme I given below:

formula VI is carried out under acid catalysed conditions, more preferably by refluxing the mixture in dichloromethane in the presence of copper(II)trifluoromethanesulfonate as described, for example, in Synlett, (1), 147-149, 2001. The respective description is hereby incorporated by reference and forms part of the disclosure.

The reaction of the compound of general formula (VII) with an optionally substituted phenyl hydrazin of general formula (VIII) is preferably carried out in a suitable reaction medium such as $C_{1-4}$-alcohols or ethers such as dioxane or tetrahydrofurane or mixtures of at least two of these aforementioned compounds. Also preferably, said reaction may be carried out in the presence of an acid, whereby the acid may be organic such as acetic acid and/or inorganic such as hydrochloric acid. Furthermore, the reaction may also be carried out in the presence of a base such as piperidine, piperazine, sodium hydroxide, potassium hydroxide, sodium methoxide or sodium ethoxide, or a mixture of at least two of these bases may also be used.

Reaction temperature as well as the duration of the reaction may vary over a broad range. Suitable reaction temperatures range from room temperature, i.e. approximately 25° C. to the Scheme I:

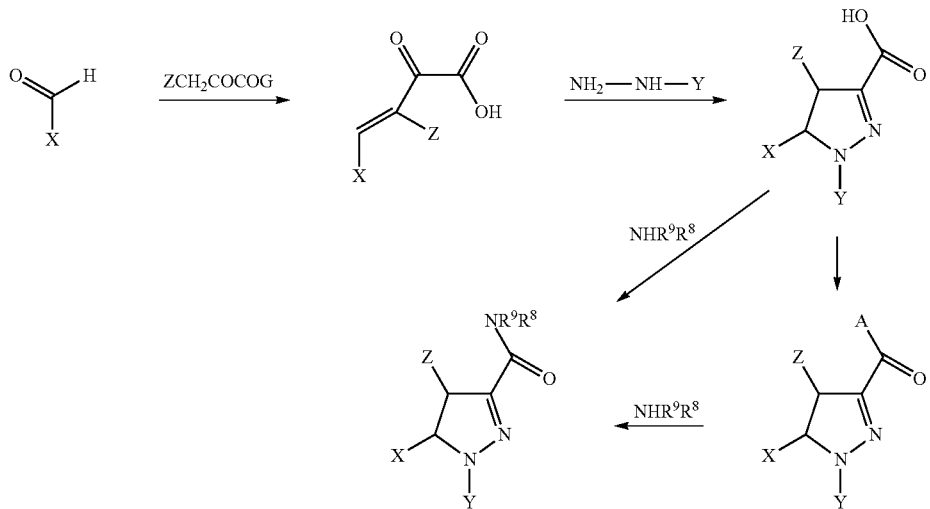

The reaction of the benzaldehyde compound of general formula V with a pyruvate compound of general formula VI is preferably carried out in the presence of at least one base, more preferably in the presence of an alkali metal hydroxide such as sodium hydroxide or potassium hydroxide or an alkali metal methoxide such as sodium methoxide, as described, for example, in Synthetic communications, 26(11), 2229-33, (1996). The respective description is hereby incorporated by reference and forms part of the disclosure. Preferably sodium pyruvate may be used as the pyruvate compound. Preferably said reaction is carried out in a protic reaction medium such as a $C_{1-4}$ alkyl alcohol or mixtures of these. Mixtures of such alcohols with water, e.g. ethanol/water may also be used.

Reaction temperature as well as the duration of the reaction may vary over a broad range. Preferred reaction temperatures range from −10° C. to the boiling point of the reaction medium. Suitable reaction times may vary for example from several minutes to several hours.

Also preferred the reaction of the benzaldehyde compound of general formula V with a pyruvate compound of general boiling point of the reaction medium. Suitable reaction times may vary for example from several minutes to several hours.

The carboxylic group of the compound of general formula (VIII) may be activated for further reactions by the introduction of a suitable leaving group according to conventional methods well known to those skilled in the art.

Preferably the compounds of general formula (IX) are transferred into an acid chloride, an acid anhydride, a mixed anhydride, a $C_{1-4}$ alkyl ester, an activated ester such as p-nitrophenylester. Other well known methods for the activation of acids include the activation with N,N-dicyclohexylcarbodiimide or benzotriazol-N-oxotris(dimethylamino)phosphonium hexafluorophosphate (BOP)).

If said activated compound of general formula (XI) is an acid chloride, it is preferably prepared by reaction of the corresponding acid of general formula (IX) with thionyl chloride or oxalyl chloride, whereby said chlorinating agent is also used as the solvent. Also preferably an additional solvent may be used. Suitable solvents include hydrocarbons such as benzene, toluene or xylene, halogenated hydrocarbons such as dichloromethane, chloroform or carbon tetrachloride, ethers such as diethyl ether, dioxane, tetrahydrofurane or dimethoxyethane. Mixtures of two or more solvents from one class or two or more solvents from different classes may also be used. Preferred reaction temperature range from 0° C. to the boiling point of the solvent and reaction times from several minutes to several hours.

If said activated compound of general formula (XI) is a mixed anhydride, said anhydride may preferably be prepared, for example, by reaction of the corresponding acid of general formula (IX) with ethyl chloroformiate in the presence of a base such as triethylamine or pyridine, in a suitable solvent.

The aforementioned reactions involving the synthesis of the 4,5-dihydro-pyrazole ring or the reaction of a compound comprising said ring are carried out under an inert atmosphere, preferably nitrogen or argon, to avoid oxidation of the ring-system.

During some synthetic reactions described above the protection of sensitive or reactive groups may be necessary and/or desirable. This can be performed by using conventional protective groups like those described in Protective groups in Organic Chemistry, ed. J. F. W. McOmie, Plenum Press, 1973; T. W. Greene & P. G. M. Wuts and Protective Groups in Organic Chemistry, John Wiley & sons, 1991. The respective parts of the description is hereby incorporated by reference and forms part of the disclosure. The protective groups may be eliminated when convenient by means well-known to those skilled in the art.

If the Indoline-substituted pyrazoline compounds of general formula I are obtained in form of a mixture of stereoisomers, particularly enantiomers or diastereomers, said mixtures may be separated by standard procedures known to those skilled in the art, e.g. chromatographic methods or crystallization with chiral reagents. It is also possible to obtain pure stereoisomers via stereoselective synthesis.

In a further aspect the present invention also provides a process for the preparation of salts of Indoline-substituted pyrazoline compounds of general formula I and stereoisomers thereof, wherein at least one compound of general formula I having at least one basic group is reacted with at least one inorganic and/or organic acid, preferably in the presence of a suitable reaction medium. Suitable reaction media include, for example, any of the ones given above. Suitable inorganic acids include hydrochloric acid, hydrobromic acid, phosphoric acid, sulfuric acid, nitric acid, suitable organic acids are e.g. citric acid, maleic acid, fumaric acid, tartaric acid, or derivatives thereof, p-toluenesulfonic acid, methanesulfonic acid or camphersulfonic acid.

In yet a further aspect the present invention also provides a process for the preparation of salts of Indoline-substituted pyrazoline compounds of general formula I or stereoisomers thereof, wherein at least one compound of general formula I having at least one acidic group is reacted with one or more suitable bases, preferably in the presence of a suitable reaction medium. Suitable bases are e.g. hydroxides, carbonates or alkoxides, which include suitable cations, derived e.g. from alkaline metals, alkaline earth metals or organic cations, e.g. $[NH_nR_{4-n}]^+$, wherein n is 0, 1, 2, 3 or 4 and R represents a branched or unbranched $C_{1-4}$-alkyl-radical. Suitable reaction media are, for example, any of the ones given above.

In the presence of several acidic or basic groups, mono- or poly-salts may be formed. Compounds of the formula I having an acidic group, for example a free carboxyl group, and a basic group, for example an amino group, may also be present in the form of inner salts, i.e., in zwitterionic form, or a part of the molecule may be present in the form of an inner salt and another part in the form of a normal salt.

Solvates, preferably hydrates, of the Indoline-substituted pyrazoline compounds of general formula I, of corresponding stereoisomers, of corresponding N-oxides or of corresponding salts thereof may also be obtained by standard procedures known to those skilled in the art.

Indoline-substituted pyrazoline compounds of general formula I, which comprise nitrogen-atom containing saturated, unsaturated or aromatic rings may also be obtained in the form of their N-oxides by methods well known to those skilled in the art.

The purification and isolation of the inventive Indoline-substituted pyrazoline compounds of general formula I, of a corresponding stereoisomer, or salt, or N-oxide, or solvate or any intermediate thereof may, if required, be carried out by conventional methods known to those skilled in the art, e.g. chromatographic methods or recrystallization.

The compounds of general formula I given above may also act as prodrugs, i.e. they represent a drug precursor, which following administration to a patient releases a drug in vivo via some kind of chemical and/or physiological process (e.g., a prodrug on being brought to a physiological pH and/or through an enzyme action is converted to a desired drug form; see, e.g., R. B. Silverman, 1992, "The Organic Chemistry of Drug Design and Drug Action", Academic Press, Chp. 8). In particular, the compounds of general formula I give rise to a compound of general formula I, wherein $R^3$ represents a —OH moiety, upon administration to a patient.

Prodrugs can be used to alter the biodistribution (e.g., to allow compounds which would not typically enter the reactive site of the protease) or the pharmacokinetics for a particular compound. For example, a hydroxyl group, can be esterified, e.g., with a carboxylic acid group to yield an ester. When the ester is administered to a subject, the ester is cleaved, enzymatically or non-enzymatically, reductively or hydrolytically, to reveal the hydroxyl group.

The Indoline-substituted pyrazoline compounds of general formula I given above, their stereoisomers, corresponding N-oxides, corresponding salts thereof and corresponding solvates are toxicologically acceptable and are therefore suitable as pharmaceutical active substances for the preparation of medicaments.

It has been found that the Indoline-substituted pyrazoline compounds of general formula I given above, stereoisomers thereof, N-oxides thereof, corresponding salts and corresponding solvates have a high affinity to cannabinoid receptors, particularly cannabinoid 1 ($CB_1$)-receptors, i.e. they are selective ligands for the ($CB_1$)-receptor and act as modulators, e.g. antagonists, inverse agonists or agonists, on these receptors. In particular, these pyrazoline compounds show little or no development of tolerance during treatment, particularly with respect to food intake, i.e. if the treatment is interrupted for a given period of time and then continued afterwards, the inventively used pyrazoline compounds will again show the desired effect. After ending the treatment with the pyrazoline compounds, the positive influence on the body weight is found to continue.

Furthermore, these Indoline-substituted pyrazoline compounds show relatively weak Herg channel affinity, thus a low risk of prolongation of the QT-interval is to be expected for these compounds.

In summary, the inventively used 4-substituted pyrazoline compounds are distinguished by a broad spectrum of beneficial effects, while at the same time showing relatively little undesired effects, i.e. effects which do not positively contribute to or even interfere with the well being of the patient.

Thus, an other aspect of the present invention relates to a medicament comprising at least one Indoline-substituted pyrazoline compound of general formula I, optionally in form of one of its stereoisomers, preferably enantiomers or diastereomers, a racemate or in form of a mixture of at least two of its stereoisomers, preferably enantiomers and/or diastereomers, in any mixing ratio, or a corresponding N-oxide thereof, or a physiologically acceptable salt thereof, or a corresponding solvate thereof, and optionally at least one physiologically acceptable auxiliary agent.

Preferably said medicament is suitable for the modulation (regulation) of cannabinoid-receptors, preferably cannabinoid 1 ($CB_1$) receptors, for the prophylaxis and/or treatment of disorders of the central nervous system, disorders of the immune system, disorders of the cardiovascular system, disorders of the endocrinous system, disorders of the respiratory system, disorders of the gastrointestinal tract or reproductive disorders.

Particularly preferably said medicament is suitable for the prophylaxis and/or treatment of psychosis.

Also particularly preferably said medicament is suitable for the prophylaxis and/or treatment of food intake disorders, preferably bulimia, anorexia, cachexia, obesity and/or type II diabetus mellitus (non-insuline dependent diabetes mellitus), more preferably obesity. The inventive medicament also seems to be active in the prophylaxis and/or treatment of appetency disorders, e.g. the pyrazoline compounds of general formula I also reduce the desire for sweets.

Also particularly preferably said medicament is suitable for the prophylaxis and/or treatment of cancer, preferably for the prophylaxis and/or treatment of one or more types of cancer selected from the group consisting of brain cancer, bone cancer, lip cancer, mouth cancer, esophageal cancer, stomach cancer, liver cancer, bladder cancer, pancreas cancer, ovary cancer, cervical cancer, lung cancer, breast cancer, skin cancer, colon cancer, bowel cancer and prostate cancer, more preferably for the prophylaxis and/or treatment of one or more types of cancer selected from the group consisting of colon cancer, bowel cancer and prostate cancer.

Particularly preferably said medicament is suitable for the prophylaxis and/or treatment of alcohol abuse and/or alcohol addiction, nicotine abuse and/or nicotine addiction, drug abuse and/or drug addiction and/or medicament abuse and/or medicament addiction, preferably drug abuse and/or drug addiction and/or nicotine abuse and/or nicotine addiction.

Medicaments and/or drugs, which are frequently the subject of misuse include opioids, barbiturates, cannabis, cocaine, amphetamines, phencyclidine, hallucinogens and benzodiazepines.

The medicament is also suitable for the prophylaxis and/or treatment of one or more disorders selected from the group consisting of bone disorders, preferably osteoporosis (e.g. osteoporosis associated with a genetic predisposition, sex hormone deficiency, or ageing), cancer-associated bone disease or Paget's disease of bone; schizophrenia, anxiety, depression, epilepsy, neurodegenerative disorders, cerebellar disorders, spinocerebellar disorders, cognitive disorders, cranial trauma, head trauma, stroke, panic attacks, peripheric neuropathy, inflammation, glaucoma, migraine, Morbus Parkinson, Morbus Huntington, Morbus Alzheimer, Raynaud's disease, tremblement disorders, compulsive disorders, senile dementia, thymic disorders, tardive dyskinesia, bipolar disorders, medicament-induced movement disorders, dystonia, endotoxemic shock, hemorrhagic shock, hypotension, insomnia, immunologic disorders, sclerotic plaques, vomiting, diarrhea, asthma, memory disorders, pruritus, pain, or for potentiation of the analgesic effect of narcotic and non-narcotic analgesics, or for influencing intestinal transit.

Another aspect of the present invention is the use of at least one Indoline-substituted pyrazoline compound of general formula I given above as suitable active substances, optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof, and optionally one or more pharmaceutically acceptable excipients, for the preparation of a medicament for the modulation of cannabinoid-receptors, preferably cannabinoid 1 ($CB_1$) receptors, for the prophylaxis and/or treatment of disorders of the central nervous system, disorders of the immune system, disorders of the cardiovascular system, disorders of the endocrinous system, disorders of the respiratory system, disorders of the gastrointestinal tract or reproductive disorders.

Particularly preferred is the use of at least one of the respective Indoline-substituted pyrazoline compounds, optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof, and optionally one or more pharmaceutically acceptable excipients, for the preparation of a medicament for the prophylaxis and/or treatment of psychosis.

Also particularly preferred is the use of at least one of the respective Indoline-substituted pyrazoline compounds, optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof, and optionally one or more pharmaceutically acceptable excipients, for the preparation of a medicament for the prophylaxis and/or treatment of food intake disorders, preferably bulimia, anorexia, cachexia, obesity and/or type II diabetus mellitus (non-insuline dependent diabetes mellitus), more preferably obesity.

Also particularly preferred is the use of at least one of the pyrazoline compounds as defined herein and optionally one or more pharmaceutically acceptable excipients, for the preparation of a medicament for the treatment of metabolic syndrome.

The metabolic syndrome and definitions thereof are described in detail by Eckel et al., The Lancet, Vol. 365 (2005), 1415-1428, included herewith by reference. One of the respective definitions was established by the WHO in 1998 (as described in Alberti et al., Diabet. Med. 1998, 15, pages 539-53, the respective description thereof is herewith incorporated by reference and forms part of the present disclosure). The other, more widely accepted, definition of the metabolic syndrome was established by the Adult Treatment Panel (ATP III) of the US National Cholesterol Education Program (NCEP) in 2001, as described in JAMA 2001; 285; 2486-97, the respective description thereof is herewith incorporated by reference and forms part of the present disclosure.

The metabolic syndrome is characterized by an interaction of several physiological parameters such as triglycerides, lipids, blood pressure, glucose levels and insuline levels.

Even though obesity may play a critical role in the development of metabolic syndrome, many of its aspects are weight independent, especially some lipid parameters. Especially the positive influence on the weight independent aspects of the metabolic syndrome (see e.g. Pagotto and Pasquali, The Lancet, Vol. 365 (2005), 1363, 1364, included herewith by reference) like some blood parameters, especially lipid parameters is one of the major and surprising advantages of the inventively used substituted pyrazoline compounds.

Another aspect of the invention is the use of one or more pyrazoline compounds as defined herein for the manufacture of a medicament for improvement of cardiovascular and/or metabolic risk factors, such as one or more of the following factors:
Elevated triglycerides, whereby elevated levels of triglycerides are preferably understood as being >150 mg/dl,
Low HDL cholesterol, whereby low levels of HDL cholesterol are preferably understood as being <40 mg/dl in men and <50 mg/dl in women,
Hypertension, whereby hypertension is preferably understood as being >130/85 mmHg,
Impaired fasting glucose, whereby impaired fasting glucose levels are preferably understood as being >110 mg/dl,
Insulin Resistance
Dyslipidemia.

Another aspect of the invention is the use of one or more pyrazoline compounds as defined herein for the manufacture of a medicament for the treatment of the weight independent aspects of metabolic syndrome.

Another aspect of the invention is a method for improving cardiovascular and/or metabolic risk factors, such as one or more of the following factors:
Elevated triglycerides, whereby elevated levels of triglycerides are preferably understood as being >150 mg/dl,
Low HDL cholesterol, whereby low levels of HDL cholesterol are preferably understood as being <40 mg/dl in men and <50 mg/dl in women,
Hypertension, whereby hypertension is preferably understood as being >130/85 mmHg,
Impaired fasting glucose, whereby impaired fasting glucose levels are preferably understood as being >110 mg/dl,
Insulin Resistance
Dyslipidemia,
in a subject, preferably a human.

Another aspect of the invention is a method for treating of the weight independent aspects of metabolic syndrome.

Also particularly preferred is the use of at least one of the respective Indoline-substituted pyrazoline compounds, optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof, and optionally one or more pharmaceutically acceptable excipients, for the preparation of a medicament for the prophylaxis and/or treatment of cancer, preferably for the prophylaxis and/or treatment of one or more types of cancer selected from the group consisting of brain cancer, bone cancer, lip cancer, mouth cancer, esophageal cancer, stomach cancer, liver cancer, bladder cancer, pancreas cancer, ovary cancer, cervical cancer, lung cancer, breast cancer, skin cancer, colon cancer, bowel cancer and prostate cancer, more preferably for the prophylaxis and/or treatment of one or more types of cancer selected from the group consisting of colon cancer, bowel cancer and prostate cancer.

Also particularly preferred is the use of at least one of the respective Indoline-substituted pyrazoline compounds, optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof, and optionally one or more pharmaceutically acceptable excipients, for the preparation of a medicament for the prophylaxis and/or treatment of alcohol abuse and/or alcohol addiction, nicotine abuse and/or nicotine addiction, drug abuse and/or drug addiction and/or medicament abuse and/or medicament addiction, preferably drug abuse and/or drug addiction and/or nicotine abuse and/or nicotine addiction.

Medicaments/drugs, which are frequently the subject of misuse include opioids, barbiturates, cannabis, cocaine, amphetamines, phencyclidine, hallucinogens and benzodiazepines.

Also preferred is the use of at least one of the respective Indoline-substituted pyrazoline compounds, optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof, and optionally one or more pharmaceutically acceptable excipients, for the preparation of a medicament for the prophylaxis and/or treatment of one or more disorders selected from the group consisting of bone disorders, preferably osteoporosis (e.g. osteoporosis associated with a genetic predisposition, sex hormone deficiency, or ageing), cancer-associated bone disease or Paget's disease of bone; schizophrenia, anxiety, depression, epilepsy, neurodegenerative disorders, cerebella disorders, spinocerebellar disorders, cognitive disorders, cranial trauma, head trauma, stroke, panic attacks, peripheric neuropathy, inflammation, glaucoma, migraine, Morbus Parkinson, Morbus Huntington, Morbus Alzheimer, Raynaud's disease, tremblement disorders, compulsive disorders, senile dementia, thymic disorders, tardive dyskinesia, bipolar disorders, medicament-induced movement disorders, dystonia, endotoxemic shock, hemorrhagic shock, hypotension, insomnia, immunologic disorders, sclerotic plaques, vomiting, diarrhea, asthma, memory disorders, pruritus, pain, or for potentiation of the analgesic effect of narcotic and non-narcotic analgesics, or for influencing intestinal transit.

The medicament according to the present invention may be in any form suitable for the application to humans and/or animals, preferably humans including infants, children and adults and can be produced by standard procedures known to those skilled in the art. The medicament can be produced by standard procedures known to those skilled in the art, e.g. from the table of contents of "Pharmaceutics: The Science of Dosage Forms", Second Edition, Aulton, M. E. (ED. Churchill Livingstone, Edinburgh (2002); "Encyclopedia of Pharmaceutical Technology", Second Edition, Swarbrick, J. and Boylan J. C. (Eds.), Marcel Dekker, Inc. New York (2002); "Modern Pharmaceutics", Fourth Edition, Banker G. S. and Rhodes C. T. (Eds.) Marcel Dekker, Inc. New York 2002 y "The Theory and Practice of Industrial Pharmacy", Lachman L., Lieberman H. And Kanig J. (Eds.), Lea & Febiger, Philadelphia (1986). The respective descriptions are hereby incorporated by reference and form part of the disclosure. The composition of the medicament may vary depending on the route of administration.

The medicament of the present invention may for example be administered parentally in combination with conventional injectable liquid carriers, such as water or suitable alcohols. Conventional pharmaceutical excipients for injection, such as stabilizing agents, solubilizing agents, and buffers, may be included in such injectable compositions. These medicaments may for example be injected intramuscularly, intraperitoneally, or intravenously.

Medicaments according to the present invention may also be formulated into orally administrable compositions containing one or more physiologically compatible carriers or excipients, in solid or liquid form. These compositions may contain conventional ingredients such as binding agents, fillers, lubricants, and acceptable wetting agents. The compositions may take any convenient form, such as tablets, pellets, granules, capsules, lozenges, aqueous or oily solutions, suspensions, emulsions, or dry powdered forms suitable for reconstitution with water or other suitable liquid medium before use, for immediate or retarded release. The multiparticulate forms, such as pellets or granules, may e.g. be filled into a capsule, compressed into tablets or suspended in a suitable liquid.

Suitable controlled release formulations, materials and methods for their preparation are known from the prior art, e.g. from the table of contents of "Modified-Release Drug Delivery Technology", Rathbone, M. J. Hadgraft, J. and Roberts, M. S. (Eds.), Marcel Dekker, Inc., New York (2002); "Handbook of Pharmaceutical Controlled Release Technology", Wise, D. L. (Ed.), Marcel Dekker, Inc. New York, (2000); "Controlled Drug Delivery", Vol, I, Basic Concepts, Bruck, S. D. (Ed.), CRD Press Inc., Boca Raton (1983) y de Takada, K. and Yoshikawa, H., "Oral Drug Delivery", Encyclopedia of Controlled Drug Delivery, Mathiowitz, E. (Ed.), John Wiley & Sons, Inc., New York (1999), Vol. 2, 728-742; Fix, J., "Oral drug delivery, small intestine and colon", Encyclopedia of Controlled Drug Delivery, Mathiowitz, E. (Ed.), John Wiley & Sons, Inc., New York (1999), Vol. 2, 698-728. The respective descriptions are hereby incorporated by reference and form part of the disclosure.

Medicaments according to the present invention may also comprise an enteric coating, so that their dissolution is dependent on pH-value. Due to said coating the medicament can pass the stomach undissolved and the respective nitro-substituted phenyl-piperazine compound is liberated in the intestinal tract. Preferably the enteric coating is soluble at a pH value of 5 to 7.5. Suitable materials and methods for the preparation are known from the prior art.

Typically, the medicaments according to the present invention may contain 1-60% by weight of one or more Indoline-substituted pyrazoline compounds as defined herein and 40-99% by weight of one or more auxiliary substances (additives).

The liquid oral forms for administration may also contain certain additives such as sweeteners, flavoring, preservatives, and emulsifying agents. Non-aqueous liquid compositions for oral administration may also be formulated, containing edible oils. Such liquid compositions may be conveniently encapsulated in e.g., gelatin capsules in a unit dosage amount.

The compositions of the present invention may also be administered topically or via a suppository.

The daily dosage for humans and animals may vary depending on factors that have their basis in the respective species or other factors, such as age, sex, weight or degree of illness and so forth. The daily dosage for humans may preferably be in the range from 1 to 2000, preferably 1 to 1500, more preferably 1 to 1000, even more preferably 1 to 150 milligrams of active substance to be administered during one or several intakes per day.

The present invention is illustrated below with the aid of examples. These illustrations are given solely by way of example and do not limit the general spirit of the present invention.

EXAMPLES

The following compounds were prepared according to the general processes described above. Those skilled in the art are familiar with the starting materials that are needed to obtain said compounds.

a) Preparation of Compound of General Formula (E)-4-(4-substituted-phenyl)-3-methyl (or 3-ethyl)-2-oxobut-3-enoic Acid

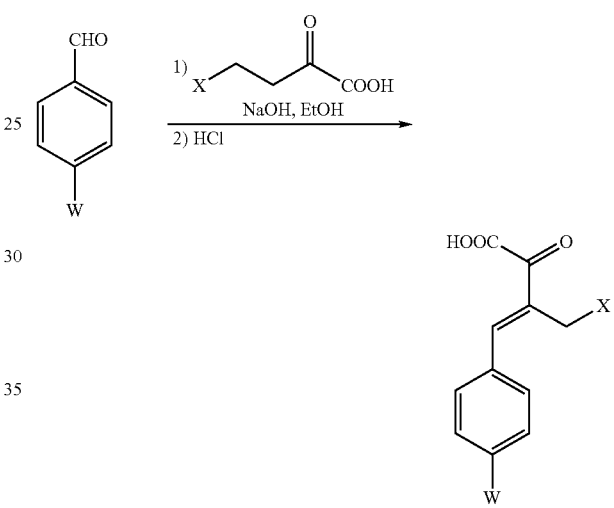

$X = H, CH_3$ (Where W has the meaning given above)

To a solution of aqueous 0.5 M NaOH (1.5 equivalents), under $N_2$ at room temperature, 2-oxobutyric acid (1.1 equivalents) is added in portions. The reaction is then left stirring for 5 min and a solution of 4-substituted-benzaldehyde (1 equivalent) in abs. EtOH (0.9 M) is then slowly added (10 mL/h). The reaction is left to stir at 25° C. overnight.

Water is added, and the solution evaporated under reduced pressure to eliminate the excess of EtOH. The solution is then washed with toluene and evaporated (to eliminate traces of this solvent). The aqueous solution is then cooled down in an ice bath and conc. HCl (0.2 mL of conc HCl per mL of base) are slowly added under magnetically stirring. A white solid precipitates from the solution which is kept at 0° C. for another hour. The solid is filtered under vacuum through a sintered funnel (porosity 3) and dried at 40° C. under vacuum.

The yield range for this aldolic condensation is 60-86%.

If the starting material is 2-oxopentanoic acid (oxovaleric acid) instead of 2-oxobutyric acid, this reaction leads to (E)-4-(4-substituted-phenyl)-3-ethyl-2-oxobut-3-enoic acids, although in this case, the yield of the reaction is slightly lower (around 40-50%)

(E)-4-(4-chlorophenyl)-3-methyl-2-oxobut-3-enoic Acid $^1$H NMR (400 MHz, CDCl$_3$): δ 2.17 (3H, s, CH$_3$), 7.44 (4H, ap d, J=3.28 Hz, ArH), 8.41 (1H, s, CH).

(E)-4-(4-bromophenyl)-3-methyl-2-oxobut-3-enoic Acid $^1$H NMR (400 MHz, CD$_3$OD): δ 1.99 (3H, s, CH$_3$), 7.36 (2H, d, J=8.5 Hz, ArH), 7.40 (1H, s, CH), 7.53 (2H, d, J=8.5 Hz, ArH).

(E)-4-(4-fluorophenyl)-3-methyl-2-oxobut-3-enoic Acid $^1$H NMR (300 MHz, DMSO-d6): δ 2.18 (3H, s, CH$_3$), 7.20 (2H, m), 7.53 (2H, m), 8.26 (1H, s, CH);

(E)-4-(4-methoxyphenyl)-3-methyl-2-oxobut-3-enoic acid. This compound is prepared following the method described above but using 3 eq of NaOH instead of 1.5 eq.

$^1$H NMR (200 MHz, CDCl$_3$): δ 2.09 (3H, s, CH$_3$), 3.84 (3H, s, OCH$_3$), 7.01 (2H, d, J=8.8 Hz, ArH), 7.50 (1H, s, CH), 7.52 (2H, d, J=8.8 Hz, ArH).

(E)-4-(4-bromophenyl)-3-ethyl-2-oxobut-3-enoic Acid $^1$H NMR (400 MHz, CDCl$_3$): δ 1.16 (3H, t, J=7.5 Hz, CH$_3$), 2.62 (2H, q, J=7.5 Hz, CH$_2$), 7.35 (2H, d, J=8.4 Hz, ArH), 7.59 (2H, d, J=8.4 Hz, ArH), 8.23 (1H, s, CH).

b) Preparation of Compound of General Formula cis or trans 5-(4-substituted-Phenyl)-1-(2,4-dichlorophenyl)-4-methyl (or 4-ethyl)-4,5-dihydro-1H-pyrazole-3-carboxylic Acid

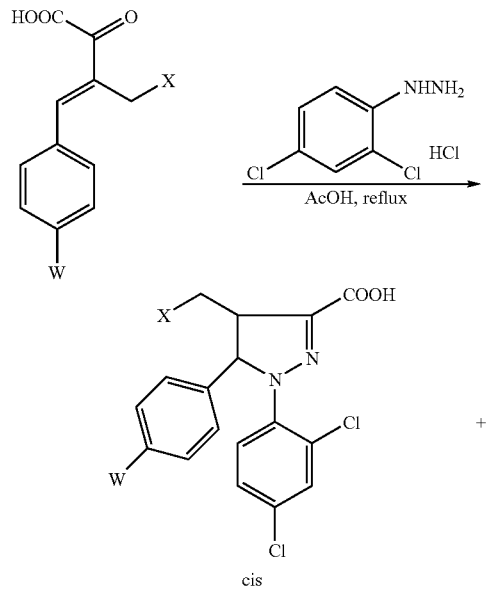

cis

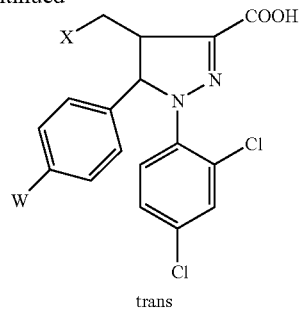

trans

X = H, CH$_3$ (Where W has the meaning given above)

A suspension of 2,4-dichlorophenylhydrazine hydrochloride (1 equivalent) in glacial acetic acid (40 equivalents) is heated at 80° C. under nitrogen atmosphere. When the suspension becomes a solution, a solution of (E)-4-(4-substituted-phenyl-3-methyl-2-oxo-3-butenoic acid (1 equivalent) in acetic acid (20 equivalents) is added and the solution left to stir at 80° C. for 2 h.

Then, the mixture can be let crystallizing at 0-4° C. overnight after some concentration of acetic acid. The beige solid formed afterwards is filtrated under vacuum through a sintered funnel (porosity 4) and washed several times with water. This crystallization process leads to the major diastereoisomeric acid cis.

The yield range for the cyclization with hydrazine to obtain the main diastereoisomer cis is around 46-60%.

If the starting material is (E)-4-(4-substituted-phenyl)-3-ethyl-2-oxobut-3-enoic acid, cis-5-(4-substituted-phenyl)-1-(2,4-dichlorophenyl)-4-ethyl-4,5-dihydro-1H-pyrazole-3-carboxylic acid is obtained. In this case, the yield for the cyclization is around 40%.

The reaction mixture can also be cooled down to room temperature and poured through an addition funnel to water, cooled in an ice bath with magnetically stirring. The addition must be slow and at least double the volume of water per volume of acetic acid is required. It should form a precipitate, but in the case a gum starts to be formed, it should be filtered and the rest of the material poured into another large volume of water. The solid obtained is suspended in water several times and filtered until the pH of the water is above 3. This solid also corresponds to the cis form.

Alternatively, the dark mixture can be extracted with dichloromethane washed thoroughly with H$_2$O, dried over Na$_2$SO$_4$ and evaporated to dryness. Recrystallisation of the crude material with toluene (3 to 4 mL of toluene per gram of material) allows the recovery of the major diastereoisomer cis.

Formation of the methyl esters, followed by purification by column chromatography, allows the separation of the two diastereoisomeric forms. Then, a hydrolysis of the pure esters gives the corresponding acids cis and trans. Example: Methyl iodide (0.16 ml, 2.25 mmol) was added dropwise to a mixture of 5-(4-chlorophenyl)-1-(2,4-dichlorophenyl)-4-methyl-4,5-dihydro-1H-pyrazole-3-carboxylic acid (0.47 g, 1.27 mmol) and KHCO$_3$ (0.19 g, 1.9 mmol) in anhydrous dimethylformamide (10 ml) under nitrogen atmosphere. The mixture was stirred at room temperature under nitrogen overnight (ca 16 h). Water was added, the mixture was extracted with ethyl acetate and the combined organic layers were thoroughly washed with aq. NaCl. After drying over Na$_2$SO$_4$ and evaporation under reduced pressure, 0.5 g of the crude product were obtained. Purification by column chromatography (SiO$_2$, 40:1 SiO$_2$, packed with 100% hexane and eluted with a gradient of 1% to 5% ethyl acetate) affords 0.045 g (9% yield) of the minor isomer (trans racemic mixture) and 0.23 g (48% yield) of the major isomer (cis racemic mixture). Hydrolysis of the esters in the presence of NaOH leads to the corresponding acids.

Another way to acids trans is described below:

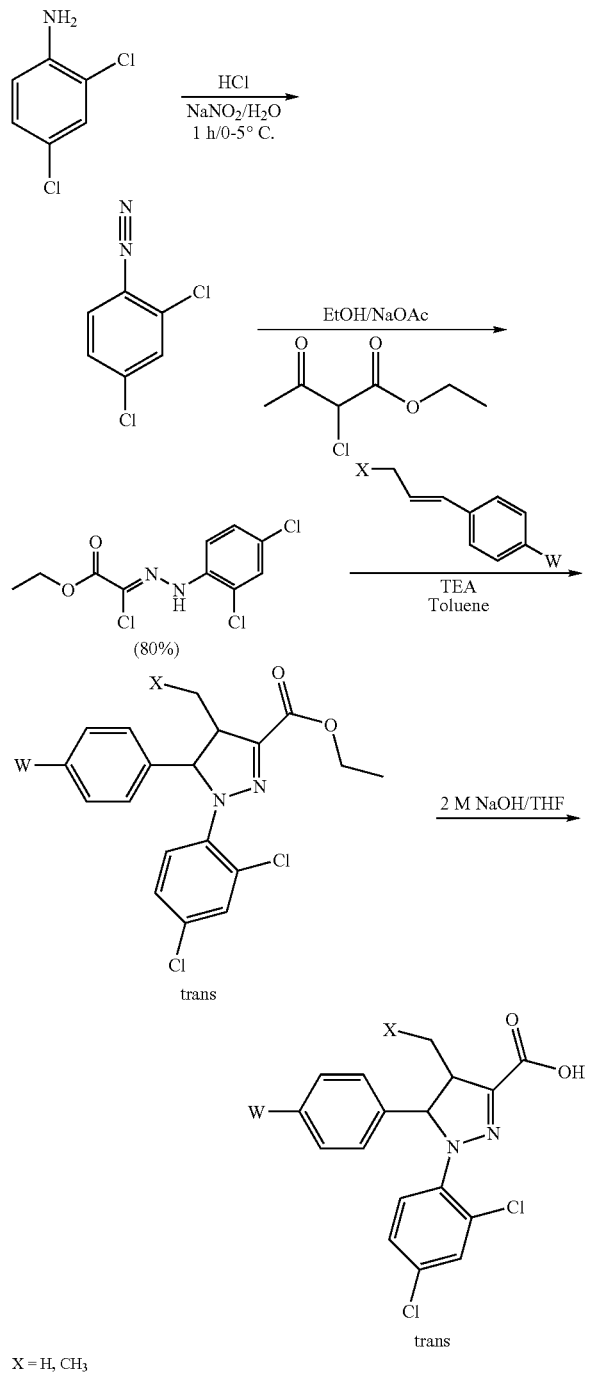

X = H, CH$_3$

To a stirred solution of 2,4-dichloroaniline (1 g, 6.17 mmol) and concentrated hydrochloric acid (1.5 ml) in ice (1.5 ml) a solution of NaNO$_2$ (0.460 mg, 6.68 mmol) in water (0.8 ml) is slowly added and the mixture is stirred for 1 h at 0-5° C. Then, this solution is added over a cold mixture of NaOAc (1.64 g, 19.6 mmol), ethanol (26 ml) and ethyl-2-chloro-3-oxobutanoate (1.0 g, 6.06 mmol) and let stirring for 1 hour until the formed precipitate is collected by filtration, washed with ethanol and dichloromethane and dried in vacuo to give the yellow solid ethyl 2-chloro-2-(2-(2,4-dichlorophenyl)hydrazono)acetate (70-80% yield), which is used in the next step without any further purification.

Then, triethylamine (2.8 eq) is added to a solution of 2-chloro-2-(2-(2,4-dichlorophenyl)hydrazono)acetate (1 eq) and a 4-substituted trans-β-methylstyrene (3 eq) in toluene, and the mixture is stirred at reflux temperature for 1 hour. The formed precipitate is removed by filtration after cooling to room temperature. The filtrate is concentrated and purified using a Combiflah system from Isco, eluting with cyclohexane and ethyl acetate (in a gradient program until 30% AcOEt), to obtain pure ethyl trans-5-(4-substituted-phenyl)-1-(2,4-dichlorophenyl)-4-methyl-4,5-dihydro-1H-pyrazole-3-carboxylate, (~40% yield). Another compound can be isolated from the purification, which is identified as the regioisomer ethyl trans-4-(4-substituted-phenyl)-1-(2,4-dichlorophenyl)-5-methyl-4,5-dihydro-1H-pyrazole-3-carboxylate (~10% yield).

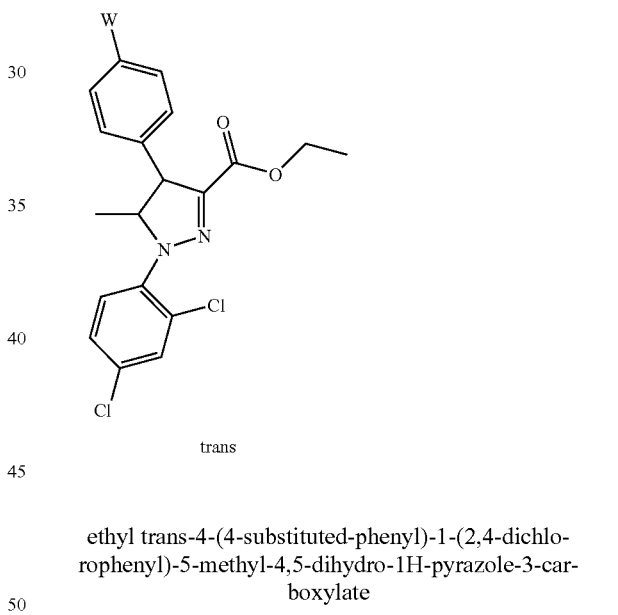

ethyl trans-4-(4-substituted-phenyl)-1-(2,4-dichlorophenyl)-5-methyl-4,5-dihydro-1H-pyrazole-3-carboxylate $^1$H NMR (300 MHz, CHLOROFORM-d) δ ppm 1.00 (d, J=6.6 Hz, 3H) 1.18 (t, J=7.2 Hz, 3H) 4.06 (d, J=3.3 Hz, 1H) 4.16 (m, 2H) 4.91 (m, 1H) 7.10-7.45 (m, 8H)

Ethyl trans-5-(4-substituted-phenyl)-1-(2,4-dichlorophenyl)-4-methyl-4,5-dihydro-1H-pyrazole-3-carboxylate is hydrolyzed in the presence of aqueous 2 M NaOH (2 eq) and tetrahydrofuran for 4 hours. Then, tetrahydrofuran is partially removed by evaporation, 1 M HCl is added until pH is below 3 and the aqueous mixture is extracted with ethyl acetate, dried over Na$_2$SO$_4$, filtered and concentrated in vacuo to yield a white solid identified as trans-5-(4-substituted-phenyl)-1-(2,4-dichlorophenyl)-4-methyl-4,5-dihydro-1H-pyrazole-3-carboxylic acid (85% yield). The resgioisomer ethyl trans-4-(4-substituted-phenyl)-1-(2,4-dichlorophenyl)-5-methyl-4,5-dihydro-1H-pyrazole-3-carboxylate can be hydrolyzed in the same way.

The two enantiomers of each acid (cis or trans) can be separated by chiral HPLC or by crystallization of the diastereoisomeric salts formed with chiral amines.

cis-5-(4-chlorophenyl)-1-(2,4-dichlorophenyl)-4-methyl-4,5-dihydro-1H-pyrazole-3-carboxylic Acid IR (KBr, cm$^{-1}$): 2976, 1682, 1566, 1542, 1490, 1270, 1242, 1117.

$^1$H NMR (400 MHz, CHLOROFORM-d) δ ppm 0.96 (d, J=7.42 Hz, 3H) 3.82 (td, J=11.72, 7.42 Hz, 1H) 5.91 (d, J=11.72 Hz, 1H) 7.04 (d, J=8.60 Hz, 2H) 7.11 (dd, J=8.60, 2.34 Hz, 1H) 7.21-7.30 (m, 4H)

$^{13}$C NMR (100 MHz, CDCl$_3$): δ 13.6 (CH$_3$), 43.5 (CH), 72.0 (CH), 124.9 (CH), 127.6 (CH), 129.1 (CH), 129.6 (CH), 130.9 (CH), 131.3 (C), 132.7 (C), 134.5 (C), 138.7 (C), 144.6 (C), 165.9 (CO).

cis-5-(4-bromophenyl)-1-(2,4-dichlorophenyl)-4-methyl-4,5-dihydro-1H-pyrazole-3-carboxylic Acid IR (KBr, cm$^{-1}$): 2976, 1683, 1541, 1486, 1385, 1270, 1242, 1116.

$^1$H NMR (400 MHz, CDCl$_3$): δ 0.96 (3H, d, J=7.3 Hz, CH$_3$), 3.82 (1H, qd, J=11.9, 7.3, 7.3, 7.3 Hz, 1H), 5.88 (1H, d, J=11.9 Hz, CH), 6.99 (2H, ap d, J=8.4 Hz, ArH), 7.12 (1H, dd, J=8.7, 2.3 Hz, 1H), 7.17 (1H, m, ArH), 7.27 (1H, m, ArH), 7.39 (2H, d, J=8.4 Hz, ArH).

cis-5-(4-fluorophenyl)-1-(2,4-dichlorophenyl)-4-methyl-4,5-dihydro-1H-pyrazole-3-carboxylic Acid IR (KBr, cm$^{-1}$): 2978, 1682, 1486, 1471, 1264, 1117.

$^1$H NMR (400 MHz, CHLOROFORM-d) δ ppm 0.97 (d, J=7.42 Hz, 3H) 3.82 (td, J=11.72, 7.42 Hz, 1H) 5.91 (d, J=12.0 Hz, 1H), 6.95 (m, 2H), 7.10 (m, 3H), 7.20 (d, J=9.0 Hz, 1H), 7.30 (d, J=3.0 Hz, 1H).

cis-5-(4-methoxyphenyl)-1-(2,4-dichlorophenyl)-4-methyl-4,5-dihydro-1H-pyrazole-3-carboxylic Acid IR (KBr, cm$^{-1}$): 2936, 2836, 1681, 1612, 1512, 1480, 1460, 1248, 1113.

$^1$H NMR (400 MHz, CDCl$_3$): δ 0.97 (3H, d, J=7.3 Hz, CH$_3$), 3.74 (3H, s, OCH$_3$), 3.80 (1H, m, 1H), 5.88 (1H, d, J=11.8 Hz, CH), 6.76 (2H, ap d, J=8.6 Hz, ArH), 7.00 (2H, d, J=8.6, ArH), 7.09 (1H, dd, J=8.6, 2.3 Hz, ArH), 7.16-7.28 (2H, m, ArH).

cis-5-(4-bromophenyl)-1-(2,4-dichlorophenyl)-4-ethyl-4,5-dihydro-1H-pyrazole-3-carboxylic Acid IR (KBr, cm$^{-1}$): 2969, 1682, 1480, 1452, 1270, 1236, 1151, 1106.

$^1$H NMR (400 MHz, CDCl$_3$): δ 0.69 (3H, t, J=7.4 Hz, CH$_3$), 1.28-1.34 (1H, m, CHH), 1.95-2.00 (1H, m, CHH, 3.68 (1H, ddd, J=11.5, 9.7, 4.0 Hz, CH), 5.92 (1H, d, J=11.5 Hz, CH), 7.02 (2H, ap d, J=8.4 Hz, ArH), 7.09 (1H, dd, J=8.7, 2.4 Hz, ArH), 7.20 (1H, d, J=8.7 Hz, ArH), 7.28 (1H, d, J=2.4 Hz, ArH), 7.36 (2H, ap d, J=8.4 Hz, ArH);

$^{13}$C NMR (100 MHz, CDCl$_3$): δ 12.4 (CH$_3$), 20.0 (CH$_2$), 50.5 (CH$_3$), 52.3 (OCH$_3$), 72.0 (CH), 122.5 (C), 124.8 (CH), 127.4 (C), 127.5 (CH), 129.9 (CH), 130.4 (CH), 131.1 (C), 131.7 (CH), 132.7 (C), 138.5 (C), 143.8 (C), 165.4 (CO).

trans-5-(4-chlorophenyl)-1-(2,4-dichlorophenyl)-4-methyl-4,5-dihydro-1H-pyrazole-3-carboxylic Acid $^1$H NMR (400 MHz, CHLOROFORM-d) δ ppm 1.52 (d, J=7.03 Hz, 3H) 3.52 (m, 1H) 5.39 (d, J=5.47 Hz, 1H) 7.08 (ddd, J=13.92, 5.62, 5.28 Hz, 3H) 7.14-7.34 (m, 4H)

$^{13}$C NMR (100 MHz, CDCl$_3$): δ 18.4 (CH$_3$), 48.9 (CH), 76.2 (CH), 126.4 (CH), 126.7 (C), 127.8 (CH), 128.0 (CH), 129.5 (CH), 130.5 (CH), 131.5 (C), 134.7 (C), 137.6 (C), 138.6 (C), 144.2 (C), 166.5 (CO).

trans-5-(4-bromophenyl)-1-(2,4-dichlorophenyl)-4-methyl-4,5-dihydro-1H-pyrazole-3-carboxylic Acid $^1$H NMR (400 MHz, CDCl$_3$): δ 1.52 (3H, d, J=7.1 Hz, CH$_3$), 3.52 (1H, m, 1H), 5.35 (1H, d, J=5.8 Hz, CH), 7.00 (2H, ap d, J=8.4 Hz, ArH), 7.10 (1H, dd, J=8.7, 2.3 Hz, 1H), 7.22 (1H, d, J=8.7, ArH), 7.27 (1H, d, J=2.3 Hz, ArH), 7.37 (2H, d, J=8.4 Hz, ArH).

(c) cis or trans 5-(4-substituted-phenyl)-1-(2,4-dichlorophenyl)-4-methyl (or 4-ethyl)-4,5-dihydro-1H-pyrazole-3-carbonyl Chloride

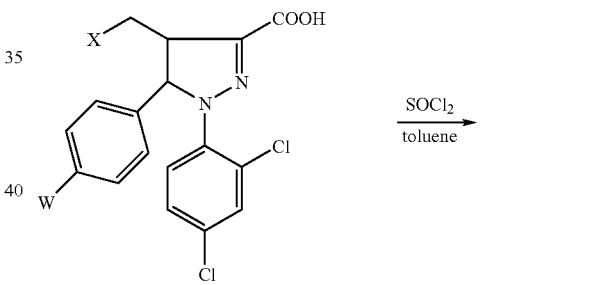

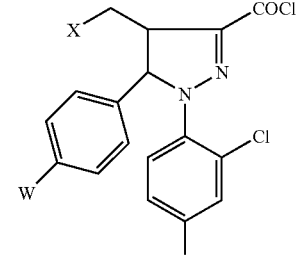

X = H, CH$_3$ (Where W has the meaning given above)

cis or trans 5-(4-substituted-phenyl)-1-(2,4-dichlorophenyl)-4-methyl (or 4-ethyl)-4,5-dihydro-1H-pyrazole-3-carboxylic acid (15 mmols) obtained according to step (b) was dissolved in 120 mL of dry toluene and thionyl chloride (18 mmols) was added. The mixture is heated to 80° C. for 2.5 hours. The solvent is removed under reduced pressure and the resulting crude residue is used without any further purification.

cis-5-(4-chlorophenyl)-1-(2,4-dichlorophenyl)-4-methyl-4,5-dihydro-1H-pyrazole-3-carbonyl Chloride IR (KBr, cm$^{-1}$): 1732, 1700, 1533, 1478, 1212, 826.

cis-5-(4-bromophenyl)-1-(2,4-dichlorophenyl)-4-methyl-4,5-dihydro-1H-pyrazole-3-carbonyl Chloride IR (KBr, cm$^{-1}$): 1731, 1527, 1477, 1204, 1153, 1132, 825, 802.

cis-5-(4-fluorophenyl)-1-(2,4-dichlorophenyl)-4-methyl-4,5-dihydro-1H-pyrazole-3-carbonyl Chloride IR (KBr, cm$^{-1}$): 1731, 1509, 1478, 1227, 1153, 1132, 853, 803.

cis-5-(4-methoxyphenyl)-1-(2,4-dichlorophenyl)-4-methyl-4,5-dihydro-1H-pyrazole-3-carbonyl Chloride IR (KBr, cm$^{-1}$): 1730, 1611, 1512, 1477, 1271, 1250, 1034, 831, 800.

cis-5-(4-bromophenyl)-1-(2,4-dichlorophenyl)-4-ethyl-4,5-dihydro-1H-pyrazole-3-carbonyl Chloride IR (KBr, cm$^{-1}$): 1728, 1526, 1478, 1227, 1200, 1153, 1129, 834, 801.

d) cis or trans 5-(4-substituted-phenyl)-1-(2,4-dichlorophenyl)-N-(indolin-1-yl)-4-methyl (or ethyl)-4,5-dihydro-1H-pyrazole-3-carboxamide or (5-(4-substituted-phenyl)-1-(2,4-dichlorophenyl)-4-methyl (or ethyl)-4,5-dihydro-1H-pyrazol-3-yl)(indolin-1-yl)methanone

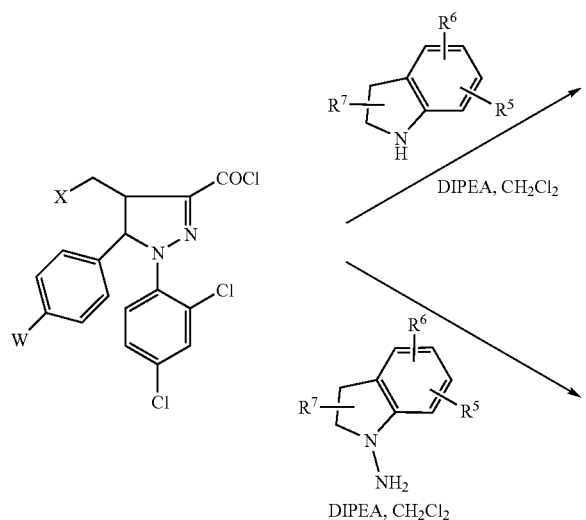

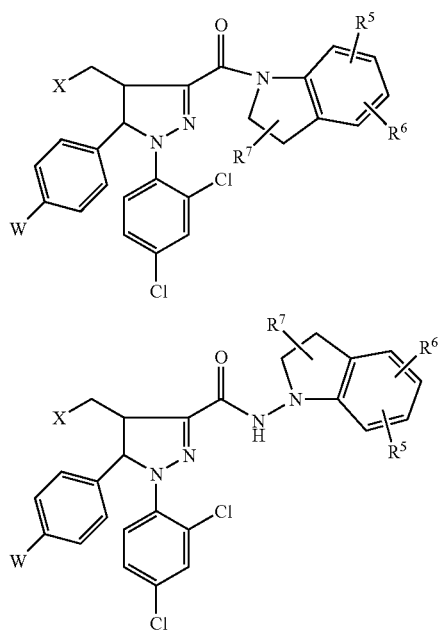

X = H, CH$_3$ (Where W, R$^5$, R$^6$ and R$^7$ have the meaning given above)

Under nitrogen atmosphere the indoline or indolin-1-amine (5.6 mmoles) and triethylamine (4 mL) were dissolved in methylene chloride (25 mL). The resulting mixture was ice-cooled down to 0° C. and a solution of cis or trans 5-(4-substituted-phenyl)-1-(2,4-dichlorophenyl)-4-methyl (or ethyl)-4,5-dihydro-1H-pyrazole-3-carbonyl chloride (4.6 mmoles) obtained in step (c) in methylene chloride (15 mL) was added dropwise. The resulting reaction mixture was stirred at room temperature (approximately 25° C.) overnight. Afterwards the reaction mixture was washed with water, followed by a saturated aqueous solution of sodium bicarbonate, then again with water, dried over sodium sulfate, filtered and evaporated to dryness in a rotavapor. The resulting crude was crystallized from ethanol or ethyl acetate. The crystallized solid was removed via filtration and the mother liquors were concentrated to yield a second fraction of crystallized product. The two fractions were combined to give the desired product (yield range: 60-80%).

If the starting material in step c) is a chiral acid, the starting configuration and ee are maintained in the final compounds.

Compounds where W=OH are prepared from the corresponding compounds with W=OMe by a cleavage with 2 M boron tribromide in dichloromethane (~75% yield)

Example 1 cis-5-(4-chlorophenyl)-1-(2,4-dichlorophenyl)-N-(indolin-1-yl)-4-methyl-4,5-dihydro-1H-pyrazole-3-carboxamide (1)

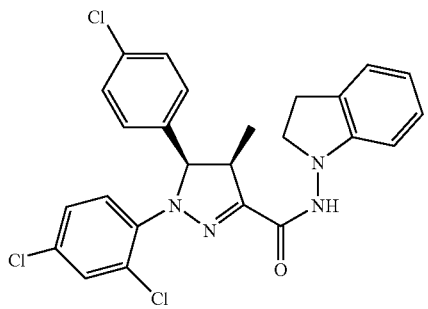

1H NMR (300 MHz, CHLOROFORM-d): δ ppm 0.97 (d, J=7.18 Hz, 3H) 3.08 (t, J=7.98 Hz, 2H) 3.67 (t, J=7.98 Hz, 2H) 3.86 (dd, J=11.06, 7.40 Hz, 1H) 5.69 (d, J=11.28 Hz, 1H) 6.73 (d, J=7.76 Hz, 1H) 6.88 (t, J=7.40 Hz, 1H) 7.02-7.12 (m, 5H) 7.15 (d, J=7.76 Hz, 2H) 7.24 (s, 1H) 7.33 (d, J=1.61 Hz, 1H) 7.99 (s, 1H)

Example 2 cis-5-(4-chlorophenyl)-1-(2,4-dichlorophenyl)-4-methyl-N-(2-methylindolin-1-yl)-4,5-dihydro-1H-pyrazole-3-carboxamide (5)

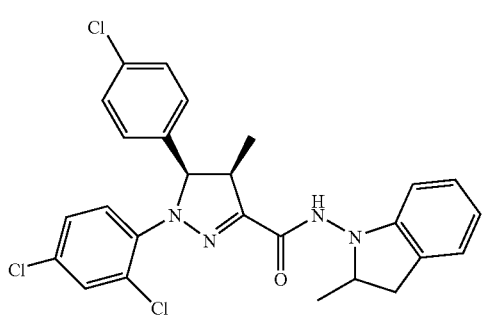

1H NMR (300 MHz, DMSO-d$_6$): δ ppm 0.81 (t, J=7.40 Hz, 3H) 1.29 (d, J=5.86 Hz, 3H) 2.54-2.65 (m, 1H) 3.14 (m, 1H) 3.92 (m, 2H) 5.99 (d, J=11.28 Hz, 1H) 6.45 (dd, J=7.54, 2.86 Hz, 1H) 6.68-6.82 (m, 1H) 6.96-7.23 (m, 4H) 7.30-7.36 (m, 3H) 7.48 (d, J=2.05 Hz, 1H) 7.71 (d, J=8.79 Hz, 1H) 10.09 (s, 1H)

Example 3 cis-5-(4-bromophenyl)-1-(2,4-dichlorophenyl)-N-(indolin-1-yl)-4-methyl-4,5-dihydro-1H-pyrazole-3-carboxamide (6)

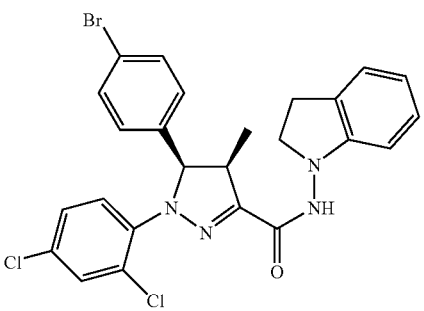

1H NMR (300 MHz, DMSO-d$_6$): δ ppm 0.80 (d, J=7.18 Hz, 3H) 2.96 (t, J=8.50 Hz, 2H) 3.59 (t, J=8.50 Hz, 2H) 3.89 (dd, J=11.13, 7.18 Hz, 1H) 5.95 (d, J=11.13 Hz, 1H) 6.49 (d, J=7.62 Hz, 1H) 6.75 (t, J=7.03 Hz, 1H) 6.99-7.14 (m, 4H) 7.31 (dd, J=8.79, 2.49 Hz, 1H) 7.42-7.50 (m, 3H) 7.66 (d, J=8.79 Hz, 1H) 10.19 (s, 1H)

Example 4 cis-1-(2,4-dichlorophenyl)-5-(4-fluorophenyl)-N-(indolin-1-yl)-4-methyl-4,5-dihydro-1H-pyrazole-3-carboxamide (8)

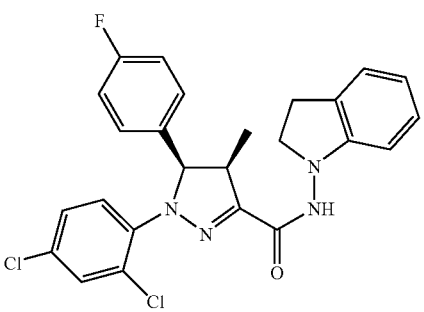

1H NMR (300 MHz, DMSO-d$_6$) δ ppm 0.80 (d, J=7.32 Hz, 3H) 2.96 (t, J=8.50 Hz, 2H) 3.59 (t, J=8.50 Hz, 2H) 3.87 (dd, J=11.13, 7.32 Hz, 1H) 5.96 (d, J=11.13 Hz, 1 H) 6.49 (d, J=7.62 Hz, 1H) 6.75 (t, J=7.40 Hz, 1H) 7.00-7.19 (m, 6H) 7.30 (dd, J=8.72, 2.42 Hz, 1H) 7.47 (d, J=2.34 Hz, 1H) 7.67 (d, J=8.79 Hz, 1H) 10.18 (s, 1H).

| N° | STRUCTURE | Autonom | ¹H-NMR | MS (M + H)⁺ |
|---|---|---|---|---|
| 1 | 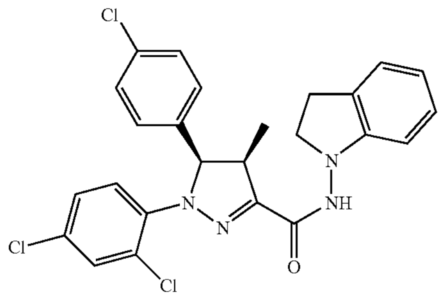 | cis-5-(4-chlorophenyl)-1-(2,4-dichlorophenyl)-N-(indolin-1-yl)-4-methyl-4,5-dihydro-1H-pyrazole-3-carboxamide | 1 H NMR (300 MHz, CHLOROFORM-d) δ ppm 0.97 (d, J = 7.18 Hz, 3 H) 3.08 (t, J = 7.98 Hz, 2 H) 3.67 (t, J = 7.98 Hz, 2 H) 3.86 (dd, J = 11.06, 7.40 Hz, 1 H) 5.69 (d, J = 11.28 Hz, 1 H) 6.73 (d, J = 7.76 Hz, 1 H) 6.88 (t, J = 7.40 Hz, 1 H) 7.02-7.12 (m, 5 H) 7.15 (d, J = 7.76 Hz, 2 H) 7.24 (s, 1 H) 7.33 (d, J = 1.61 Hz, 1 H) 7.99 (s, 1 H) | 499 |
| 2 | 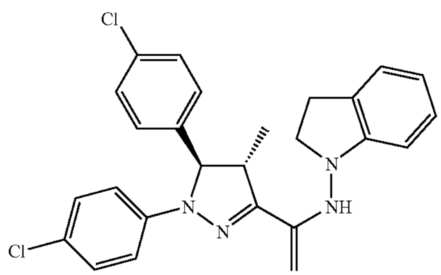 | trans-5-(4-chlorophenyl)-1-(2,4-dichlorophenyl)-N-(indolin-1-yl)-4-methyl-4,5-dihydro-1H-pyrazole-3-carboxamide | | 499 |
| 3 | 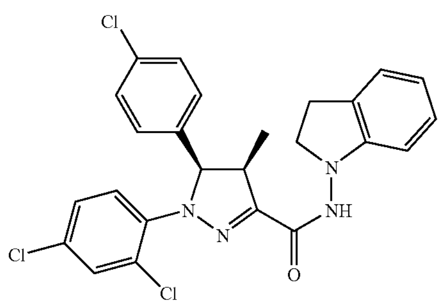 | (4R,5R)-5-(4-chlorophenyl)-1-(2,4-dichlorophenyl)-N-(indolin-1-yl)-4-methyl-4,5-dihydro-1H-pyrazole-3-carboxamide | 1 H NMR (300 MHz, CHLOROFORM-d) δ ppm 0.97 (d, J = 7.18 Hz, 3 H) 3.08 (t, J = 7.98 Hz, 2 H) 3.67 (t, J = 7.98 Hz, 2 H) 3.86 (dd, J = 11.06, 7.40 Hz, 1 H) 5.69 (d, J = 11.28 Hz, 1 H) 6.73 (d, J = 7.76 Hz, 1 H) 6.88 (t, J = 7.40 Hz, 1 H) 7.02-7.12 (m, 5 H) 7.15 (d, J = 7.76 Hz, 2 H) 7.24 (s, 1 H) 7.33 (d, J = 1.61 Hz, 1 H) 7.99 (s, 1 H) | 499 |
| 4 | 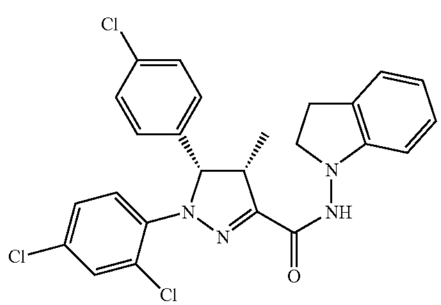 | (4S,5S)-5-(4-chlorophenyl)-1-(2,4-dichlorophenyl)-N-(indolin-1-yl)-4-methyl-4,5-dihydro-1H-pyrazole-3-carboxamide | 1 H NMR (300 MHz, CHLOROFORM-d) δ ppm 0.97 (d, J = 7.18 Hz, 3 H) 3.08 (t, J = 7.98 Hz, 2 H) 3.67 (t, J = 7.98 Hz, 2 H) 3.86 (dd, J = 11.06, 7.40 Hz, 1 H) 5.69 (d, J = 11.28 Hz, 1 H) 6.73 (d, J = 7.76 Hz, 1 H) 6.88 (t, J = 7.40 Hz, 1 H) 7.02-7.12 (m, 5 H) 7.15 (d, J = 7.76 Hz, 2 H) 7.24 (s, 1 H) 7.33 (d, J = 1.61 Hz, 1 H) 7.99 (s, 1 H) | 499 |
| 5 | 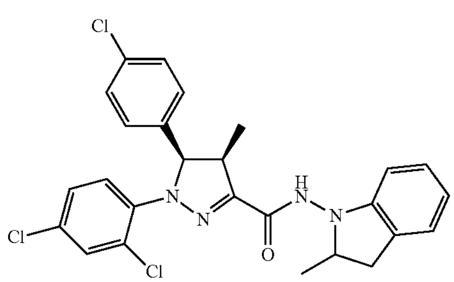 | cis-5-(4-chlorophenyl)-1-(2,4-dichlorophenyl)-4-methyl-N-(2-methylindolin-1-yl)-4,5-dihydro-1H-pyrazole-3-carboxamide | 1 H NMR (300 MHz, DMSO-d₆) δ ppm 0.81 (t, J = 7.40 Hz, 3 H) 1.29 (d, J = 5.86 Hz, 3 H) 2.54-2.65 (m, 1 H) 3.14 (m, 1 H) 3.92 (m, 2 H) 5.99 (d, J = 11.28 Hz, 1 H) 6.45 (dd, J = 7.54, 2.86 Hz, 1 H) 6.68-6.82 (m, 1 H) 6.96-7.23 (m, 4 H) 7.30-7.36 (m, 3 H) 7.48 (d, J = 2.05 Hz, 1 H) 7.71 (d, J = 8.79 Hz, 1 H) 10.09 (s, 1 H) | 513 |

-continued

| N° | STRUCTURE | Autonom | ¹H-NMR | MS (M + H)⁺ |
|---|---|---|---|---|
| 6 | 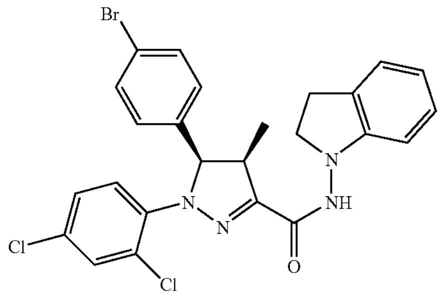 | cis-5-(4-bromophenyl)-1-(2,4-dichlorophenyl)-N-(indolin-1-yl)-4-methyl-4,5-dihydro-1H-pyrazole-3-carboxamide | 1 H NMR (300 MHz, DMSO-d₆) δ ppm 0.80 (d, J = 7.18 Hz, 3 H) 2.96 (t, J = 8.50 Hz, 2 H) 3.59 (t, J = 8.50 Hz, 2 H) 3.89 (dd, J = 11.13, 7.18 Hz, 1 H) 5.95 (d, J = 11.13 Hz, 1 H) 6.49 (d, J = 7.62 Hz, 1 H) 6.75 (t, J = 7.03 Hz, 1 H) 6.99-7.14 (m, 4 H) 7.31 (dd, J = 8.79, 2.49 Hz, 1 H) 7.42-7.50 (m, 3 H) 7.66 (d, J = 8.79 Hz, 1 H) 10.19 (s, 1 H) | 543 |
| 7 | 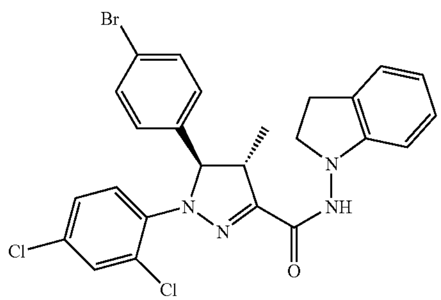 | trans-5-(4-bromophenyl)-1-(2,4-dichlorophenyl)-N-(indolin-1-yl)-4-methyl-4,5-dihydro-1H-pyrazole-3-carboxamide | | 543 |
| 8 | 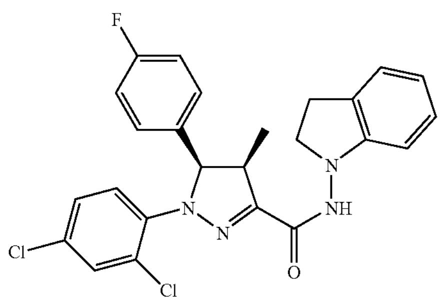 | cis-1-(2,4-dichlorophenyl)-5-(4-fluorophenyl)-N-(indolin-1-yl)-4-methyl-4,5-dihydro-1H-pyrazole-3-carboxamide | 1 H NMR (300 MHz, DMSO-d₆) δ ppm 0.80 (d, J = 7.32 Hz, 3 H) 2.96 (t, J = 8.50 Hz, 2 H) 3.59 (t, J = 8.50 Hz, 2 H) 3.87 (dd, J = 11.13, 7.32 Hz, 1 H) 5.96 (d, J = 11.13 Hz, 1 H) 6.49 (d, J = 7.62 Hz, 1 H) 6.75 (t, J = 7.40 Hz, 1 H) 7.00-7.19 (m, 6 H) 7.30 (dd, J = 8.72, 2.42 Hz, 1 H) 7.47 (d, J = 2.34 Hz, 1 H) 7.67 (d, J = 8.79 Hz, 1 H) 10.18 (s, 1 H) | 483 |
| 9 | 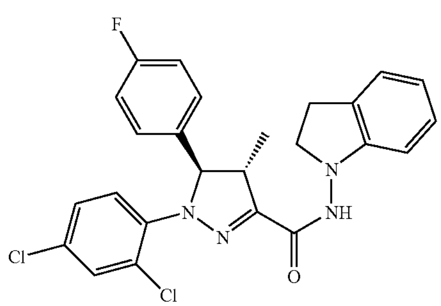 | trans-1-(2,4-dichlorophenyl)-5-(4-fluorophenyl)-N-(indolin-1-yl)-4-methyl-4,5-dihydro-1H-pyrazole-3-carboxamide | | 483 |
| 10 | 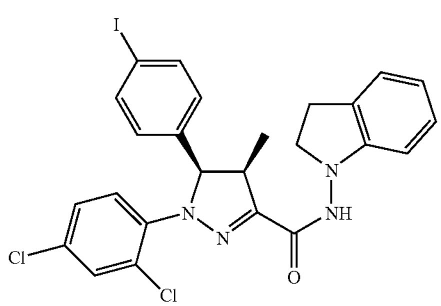 | cis-1-(2,4-dichlorophenyl)-N-(indolin-1-yl)-5-(4-iodophenyl)-4-methyl-4,5-dihydro-1H-pyrazole-3-carboxamide | | 591 |

-continued

| N° | STRUCTURE | Autonom | ¹H-NMR | MS (M + H)⁺ |
|---|---|---|---|---|
| 11 | 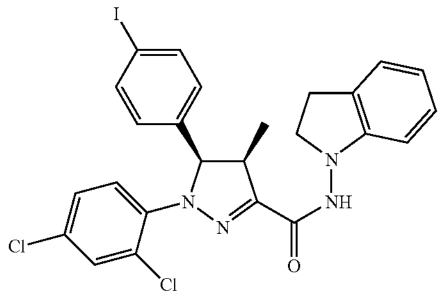 | trans-1-(2,4-dichlorophenyl)-N-(indolin-1-yl)-5-(4-iodophenyl)-4-methyl-4,5-dihydro-1H-pyrazole-3-carboxamide | | 591 |
| 12 | 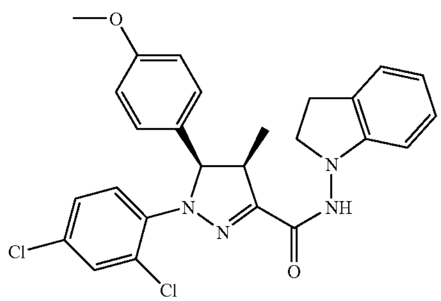 | cis-1-(2,4-dichlorophenyl)-N-(indolin-1-yl)-5-(4-methoxyphenyl)-4-methyl-4,5-dihydro-1H-pyrazole-3-carboxamide | | 495 |
| 13 | 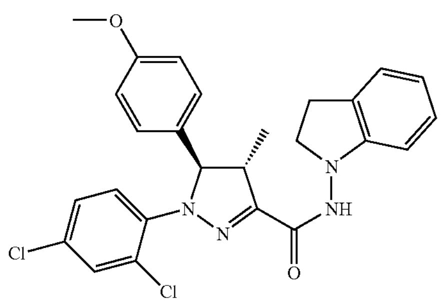 | trans-1-(2,4-dichlorophenyl)-N-(indolin-1-yl)-5-(4-methoxyphenyl)-4-methyl-4,5-dihydro-1H-pyrazole-3-carboxamide | | 495 |
| 14 | 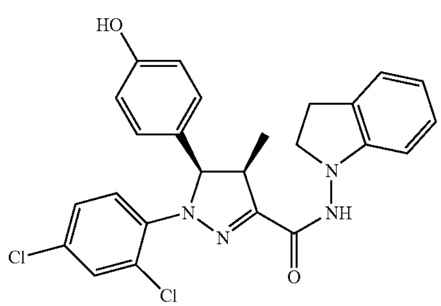 | cis-1-(2,4-dichlorophenyl)-5-(4-hydroxyphenyl)-N-(indolin-1-yl)-4-methyl-4,5-dihydro-1H-pyrazol-3-carboxamide | | 481 |
| 15 | 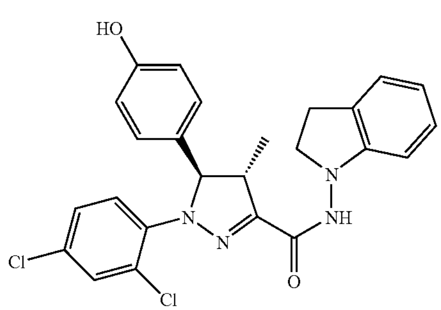 | trans-1-(2,4-dichlorophenyl)-5-(4-hydroxyphenyl)-N-(indolin-1-yl)-4-methyl-4,5-dihydro-1H-pyrazole-3-carboxamide | | 481 |

| N° | STRUCTURE | Autonom | ¹H-NMR | MS (M + H)⁺ |
|---|---|---|---|---|
| 16 | 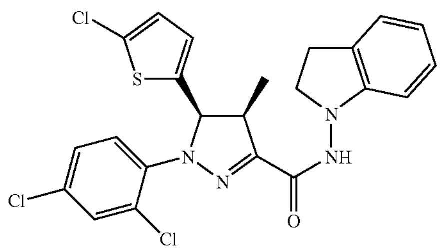 | cis-5-(5-chlorothiophen-2-yl)-1-(2,4-dichlorophenyl)-N-(indolin-1-yl)-4-methyl-4,5-dihydro-1H-pyrazole-3-carboxamide | | 505 |
| 17 | 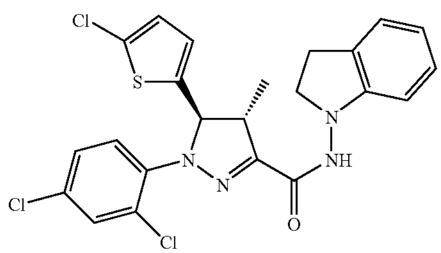 | trans-5-(5-chlorothiophen-2-yl)-1-(2,4-dichlorophenyl)-N-(indolin-1-yl)-4-methyl-4,5-dihydro-1H-pyrazole-3-carboxamide | | 505 |
| 18 | 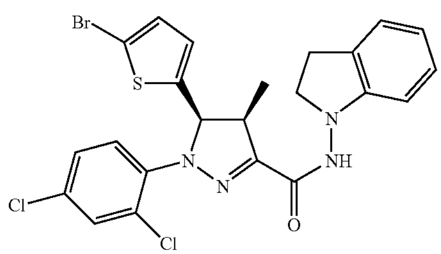 | cis-5-(5-bromothiophen-2-yl)-1-(2,4-dichlorophenyl)-N-(indolin-1-yl)-4-methyl-4,5-dihydro-1H-pyrazole-3-carboxamide | | 551 |
| 19 | 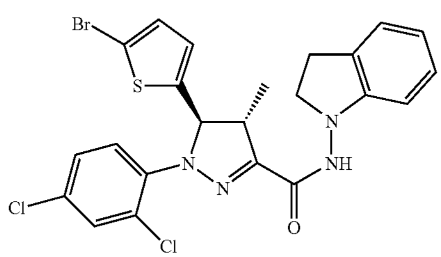 | trans-5-(5-bromothiophen-2-yl)-1-(2,4-dichlorophenyl)-N-(indolin-1-yl)-4-methyl-4,5-dihydro-1H-pyrazole-3-carboxamide | | 551 |
| 20 | 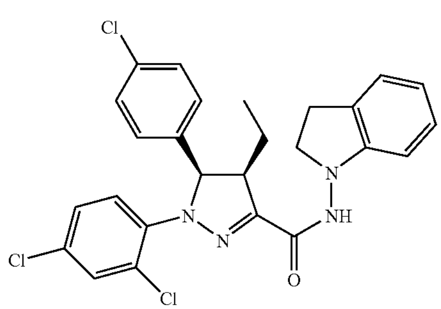 | cis-5-(4-chlorophenyl)-1-(2,4-dichlorophenyl)-4-ethyl-N-(indolin-1-yl)-4,5-dihydro-1H-pyrazole-3-carboxamide | | 513 |

| N° | STRUCTURE | Autonom | ¹H-NMR | MS (M+H)⁺ |
|---|---|---|---|---|
| 21 | 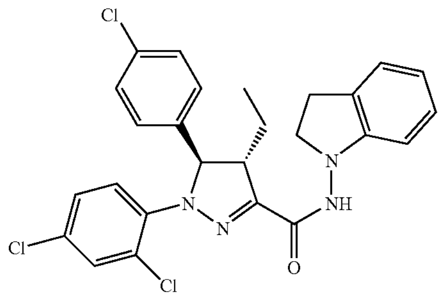 | trans-5-(4-chlorophenyl)-1-(2,4-dichlorophenyl)-4-ethyl-N-(indolin-1-yl)-4,5-dihydro-1H-pyrazole-3-carboxamide | | 513 |
| 22 | 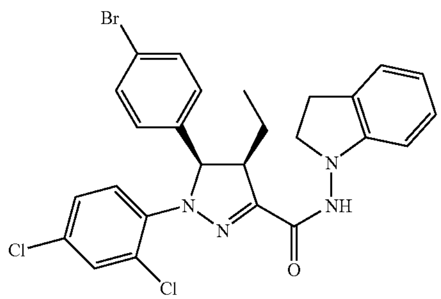 | cis-5-(4-bromophenyl)-1-(2,4-dichlorophenyl)-4-ethyl-N-(indolin-1-yl)-4,5-dihydro-1H-pyrazole-3-carboxamide | | 557 |
| 23 | 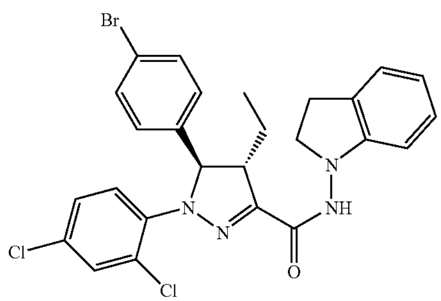 | trans-5-(4-bromophenyl)-1-(2,4-dichlorophenyl)-4-ethyl-N-(indolin-1-yl)-4,5-dihydro-1H-pyrazole-3-carboxamide | | 557 |

Pharmacological Data:

Pharmacological Methods

I. In-Vitro Determination of Affinity to CB1/CB2-Receptors

The in-vitro determination of the affinity of the inventive quaternary ammonium salts of substituted pyrazoline compounds to $CB_1/CB_2$-Rezeptors is carried out as described in the publication of Ruth A. Ross, Heather C. Brockie et al., "Agonist-inverse agonist characterization at $CB_1$ and $CB_2$ cannabinoid receptors of L-759633, L759656 and AM630", British Journal of Pharmacology, 126, 665-672, (1999), whereby the transfected human $CB_1$ and $CB_2$ receptors of Receptor Biology, Inc. are used. The radioligand used for both receptors is [³H]-CP55940. The respective parts of the description are hereby incorporated by reference and forms part of the present disclosure.

Results:

The affinity of the inventive substituted pyrazoline compounds to $CB_1/CB_2$ receptors was determined as described above. Some of the EC50-values obtained are given in the table 3 below.

As can be seen from the values given in table 3 the inventive pyrazoline compounds are particularly suitable for regulating the $CB_1$-Receptor.

II. In-Vivo Bioassay System for Determination of Cannabinoid Activity

Mouse Tetrad Model

Substances with affinity for cannabinoid receptors are known to produce a wide range of pharmacological effects. It is also known that intravenous administration of a substance with affinity for cannabinoid receptors in mice produces analgesia, hypothermia, sedation and catalepsy. Individually, none of these effects can be considered as proof that a tested substance has affinity for cannabinoid-receptors, since all of these effects are common for various classes of centrally active agents. However, substances, which show all of these effects, i.e. substances that are active in this so-called tetrad model are considered to have affinity for the cannabinoid receptors. It has further been shown that cannabinoid receptor antagonists are highly effective in blocking the effects of a cannabinoid agonist in the mouse tetrad model.

The tetrad model is described, for example, in the publication of A. C. Howlett et al, International Union of Pharmacology XXVII. Classification of Cannabinoid Receptors, Pharmacol Rev 54, 161-202, 2002 and David R. Compton et al., "In-vivo Characterization of a Specific Cannabinoid Receptor Antagonist (SR141716A): Inhibition of Tetrahydrocannbinol-induced Responses and Apparent Agonist Activity", J. Pharmacol. Exp. Ther. 277, 2, 586-594, 1996. The corresponding parts of the description are hereby incorporated by reference.

Material and Methods

Male NMRI mice with a weight of 20-30 g (Harlan, Barcelona, Spain) are used in all of the following experiments.

Before testing in the behavioral procedures given below, mice are acclimatized to the experimental setting. Pre-Treatment control values are determined for analgesia hot plate latency (in seconds), rectal temperature, sedation and catalepsy.

In order to determine the agonistic activity of the substance to be tested, the mice are injected intravenously with the substance to be tested or the vehicle alone. 15 minutes after injection, latency in hot plate analgesia is measured.

Rectal temperature, sedation and catalepsy are measured 20 minutes after injection.

In order to determine the antagonistic activity the identical procedure is used as for the determination of the agonistic effects, but with the difference that the substance to be evaluated for its antagonistic activity is injectected 5 minutes before the intravenous injection of 1.25 mg/kg Win-55,212 a known cannabinoid-receptor agonist.

Hot Plate Analgesia

The hot plate analgesia is determined according to the method described in Woolfe D. et al. "The evaluation of analgesic action of pethidine hydrochloride (Demerol)", J. Pharmacol. Exp. Ther. 80, 300-307, 1944. The respective description is hereby incorporated by reference and forms part of the present disclosure.

The mice are placed on a hot plate (Harvard Analgesimeter) at 55±0.5° C. until they show a painful sensation by licking their paws or jumping and the time for these sensations to occur is recorded. This reading is considered the basal value (B). The maximum time limit the mice are allowed to remain on the hot plate in absence of any painful response is 40 seconds in order to prevent skin damage. This period is called the cut-off time (PC).

Fifteen minutes after the administration of the substance to be tested, the mice are again placed on the hot plate and the afore described procedure is repeated. This period is called the post-treatment reading (PT).

The degree of analgesia is calculated from the formula:

$$\% \text{ MPE of Analgesia} = (PT-B)/(PC-B) \times 100$$

MPE=Maximum possible effect.

Determination of Sedation and Ataxia

Sedation and ataxia is determined according to the method described in Desmet L. K. C. et al. "Anticonvulsive properties of Cinarizine and Flunarizine in Rats and Mice", Arzneim.-Forsch. (Frug Res) 25, 9, 1975. The respective description is hereby incorporated by reference and forms part of the present disclosure.

The chosen scoring system is
0: no ataxia;
1: doubful;
2: obvious calmness and quiet;
3 pronounced ataxia;
prior to as well as after treatment.

The percentage of sedation is determined according to the formula:

$$\% \text{ of sedation} = \text{arithmetic mean}/3 \times 100$$

Hypothermia:

Hypothermia is determined according to the method described in David R. Compton et al. "In-vivo Characterization of a Specific Cannabinoid Receptor Antagonist (SR141716A) Inhibition of Tetrahydrocannbinol-induced Responses and Apparent Agonist Activity", J. Pharmacol Exp Ther. 277, 2, 586-594, 1996. The respective description is hereby incorporated by reference and forms part of the present disclosure.

The base-line rectal temperatures are determined with a thermometer (Yello Springs Instruments Co., Panlabs) and a thermistor probe inserted to 25 mm before the administration of the substance to be tested. Rectal temperature is again measured 20 minutes after the administration of the substances to be tested. The temperature difference is calculated for each animal, whereby differences of $\geq -2°$ C. are considered to represent activity.

Catalepsy:

Catalepsy is determined according to the method described in Alpermann H. G. et al. "Pharmacological effects of Hoe 249: A new potential antidepressant", Drugs Dev. Res. 25, 267-282.1992. The respective description is hereby incorporated by reference and forms part of the present disclosure.

The cataleptic effect of the substance to be tested is evaluated according to the duration of catalepsy, whereby the animals are placed head downwards with their kinlegs upon the top of the wooden block.

The chosen scoring system is:

Catalepsy for
more than 60 seconds=6; 50-60 seconds=5, 40-50 seconds=4, 30-40 seconds=3, 20-30 seconds=2, 5-10 seconds=1, and less than 5 seconds=0.

The percentage of catalepsy is determined according to the following formula:

$$\% \text{ Catalepsy} = \text{arithmetic mean}/6 \times 100$$

Antagonistic Assay:

Materials and Methods.

Membrane Preparation:

Chinese hamster ovary (CHO) cells stably expressing recombinant human cannabinoid 1 receptor (CB1) were cultured in nutrient mixture Ham's F 12 supplemented with 10% heat-inactivated fetal bovine serum, 2 mM L-glutamine, 50 U/ml penicillin, 50 U/ml streptomycin and 0.5 mg/ml geneticin. In order to obtain cells, culture flasks were washed twice with phosphate buffered saline and scraped. Then, cells were collected by centrifugation (200×g, 10 min) and stored dry at −80° C. Cells were homogenized in ice-cold 20 mM HEPES, 10 mM EDTA (pH 7.5) and centrifuged at 40,000×g for 15 min at 4° C. The pellet was resuspended in 20 mM HEPES, 0.1 mM EDTA (pH 7.5) and centrifuged for 15 min at 4° C. The final pellet was resuspended in 20 mM HEPES, 0.1 mM EDTA (pH 7.5), and divided in aliquots and stored at −80° C. until use.

[$^{35}$S]GTPγS Binding Assay:

The reaction was performed in 96-well plates. Membranes (15 □g protein/well) were incubated for 60 min at 30° C. in buffer (50 mM HEPES, 100 mM KCl, 5 mM MgCl$_2$, 1 mM EDTA, 0.1% wt/vol bovine serum albumin, 5 μM GDP, saponin (10 μg/ml), 0.5 nM [$^{35}$S]GTPγS, pH 7.4) with compound at 1 μM final concentration in either the absence or presence of dose response curve of agonist WIN 55,212-2 between 3 nM and 3 μM. The incubation was terminated by rapid filtration through Millipore Multiscreen glass fiber FB, and rinsed two-times with ice-cold assay buffer. Filter plates were dried and 30 μl of scintillation liquid was added. Radioactivity was determined using Wallac Microbeta Trilux. Each experiment was performed at least in duplicate. A WIN 55,212-2 dose-response was systematically performed.

Calculations:

The average of basal [$^{35}$S]GTPγS binding was subtracted from all binding data. In order to compare the antagonism results from one screening campaign to another one, the difference between the maximal agonist effect of WIN 55,212-2 alone, and the maximal antagonism effect due to WIN 55,212-2 with an internal standard CB1-antagonist was defined as 100%.

Results:

The determination of cannabinoid activity in-vivo was determined as described above. The antagonistic effect (against Win 55212-2) was determined for some of the compounds as given in the table 3 below:

The results of testing some of the above examples for binding and antagonism are shown together in the following table 3:

TABLE 3

| Example | IC50 (nM) | Antagonism (%) |
|---|---|---|
| 3 | 100 | 70 |
| 5 | 128.1 | 16 ± 15 |
| 7 | 39 | 67 ± 3 |
| 8 |  | 48 |

III. In Vivo Testing for Antiobesic Activity
a) Acute-Treatment

Normally handled rats are habituated to a reversed cycle 12/12 h, and the compound as well as saline is acutely orally administered. After administration the cumulated food intake (g) is measured at 6 h and 23 h. Following that the difference in body weight between control and compound treated animals is measured.

b) Long-Term-Treatment

The in-vivo testing for antiobesic activity of the inventive pyrazoline compounds is carried out as described in the publication of G. Colombo et al., "Appetite Suppression and Weight Loss after the Cannabinoid Antagonist SR 141716"; Life Sciences, 63 (8), 113-117, (1998). The respective part of the description is hereby incorporated by reference and forms part of the present disclosure.

IV. In Vivo Testing for Antidepressant Activity

The in-vivo testing for antidepressant activity of the inventive pyrazoline compounds in the water despair test is carried out as described in the publication of E. T. Tzavara et al., "The CB1 receptor antagonist SR141716A selectively increases monoaminergic neurotransmission in the medial prefrontal cortex: implications for therapeutic actions"; Br. J. Pharmacol. 2003, 138(4):544:53. The respective part of the description is hereby incorporated by reference and forms part of the present disclosure.

The invention claimed is:

1. An indoline-substituted pyrazoline compound of general formula I,

I

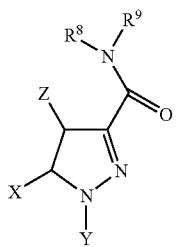

wherein

Z is $C_{1-4}$-Alkyl, wherein $C_{1-4}$-Alkyl is substituted or unsubstituted, branched or linear, or saturated or unsaturated;

X and Y independently represent phenyl, thienyl, naphthyl or pyridyl which groups may be substituted with 1, 2 or 3 substituents W, which can be the same or different, selected from the group consisting of branched or linear $C_{1-3}$-alkyl or branched or linear $C_{1-3}$-alkoxy, phenyl, hydroxy, chloro, bromo, fluoro, iodo, SH, trifluoromethyl, $CHF_2$, $CH_2F$, $OCHF_2$, trifluoromethylthio, trifluoromethoxy, methylsulfonyl, carboxyl, trifluoromethylsulfonyl, cyano, carbamoyl, sulfamoyl and acetyl; O—P, with P selected from the group consisting of aryl, $C_{8-20}$-alkyl, heteroaryl, C(O)-aryl, C(O)-heteroaryl, and C(O)—$C_{1-20}$-alkyl;

$R^8$ represents a hydrogen atom or a branched or linear $C_{1-3}$-alkyl group, while $R^9$ represents

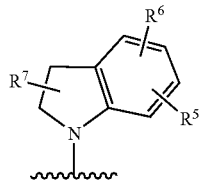

with $R^5$, $R^6$ and $R^7$ being independently from one another selected from the group consisting of H, F, Cl, Br, I, OH, SH, $C_{1-4}$alkoxy, $CF_3$, $CHF_2$, $CH_2F$, $OCF_3$, a keto-group, $NO_2$ and $NH_2$;

or $R^8$ and $R^9$ together with the connecting Nitrogen atom represent

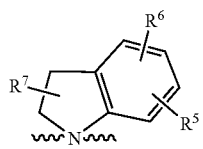

with $R^5$, $R^6$ and $R^7$ being independently from one another selected from the group consisting of H, F, Cl, Br, I, OH, SH, $C_{1-4}$alkyl, $C_{1-4}$alkoxy, $CF_3$, $CHF_2$, $CH_2F$, $OCF_3$, a keto-group, $NO_2$ and $NH_2$;

optionally in the form of a racemic mixture, a purified stereoisomer, or a mixture of stereoisomers;

in the form shown or in the form of an acid or a base or in the form of a salt, or in the form of a corresponding N-oxide thereof.

2. An indoline-substituted pyrazoline compound of general formulas Ia or Ib according to claim 1, Ia

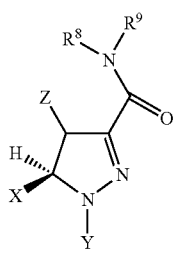

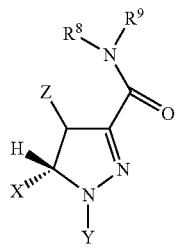

Ib wherein
Z is $C_{1-4}$-Alkyl, wherein $C_{1-4}$-Alkyl is substituted or unsubstituted, branched or linear, saturated or unsaturated;

X and Y independently represent phenyl, thienyl, naphthyl or pyridyl which groups may be substituted with 1, 2 or 3 substituents W, which can be the same or different, selected from the group consisting of:
  branched or linear $C_{1-3}$-alkyl or branched or linear $C_{1-3}$-alkoxy, phenyl, hydroxy, chloro, bromo, fluoro, iodo, SH, trifluoromethyl, $CHF_2$, $CH_2F$, $OCHF_2$, trifluoromethylthio, trifluoromethoxy, methylsulfonyl, carboxyl, trifluoromethylsulfonyl, cyano, carbamoyl, sulfamoyl and acetyl; O—P, with P selected from the group consisting of aryl, $C_{8-20}$-alkyl, heteroaryl, C(O)-aryl, C(O)-heteroaryl, C(O)—$C_{1-20}$-alkyl;

$R^8$ represents a hydrogen atom or a branched or linear $C_{1-3}$-alkyl group, while $R^9$ represents

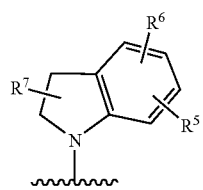

with $R^5$, $R^6$ and $R^7$ being independently from one another selected from the group consisting of H, F, Cl, Br, I, OH, SH, $C_{1-4}$alkyl, $C_{1-4}$alkoxy, $CF_3$, $CHF_2$, $CH_2F$, $OCF_3$, a keto-group, $NO_2$ and $NH_2$;

or $R^8$ and $R^9$ together with the connecting Nitrogen atom represent

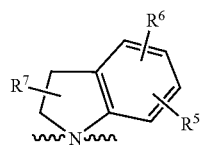

with $R^5$, $R^6$ and $R^7$ being independently from one another selected from the group consisting of H, F, Cl, Br, I, OH, SH, $C_{1-4}$alkyl, $C_{1-4}$alkoxy, $CF_3$, $CHF_2$, $CH_2F$, $OCF_3$, a keto-group, $NO_2$ and $NH_2$;

optionally in the form shown or in the form of an acid or a base or in the form of a salt, or in the form of a corresponding N-oxide thereof.

3. An indoline-substituted pyrazoline compound of general formula II according to claim 1,

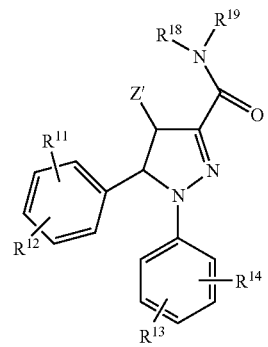

II wherein
Z' is $C_{1-4}$-Alkyl, wherein $C_{1-4}$-Alkyl is substituted or unsubstituted, branched or linear, saturated or unsaturated;

$R^{11}$, $R^{12}$, $R^{13}$ and $R^{14}$ are independently of one another selected from the group consisting of:
  H; branched or linear $C_{1-3}$-alkyl or branched or linear $C_{1-3}$-alkoxy, phenyl, hydroxy, chloro, bromo, fluoro, iodo, SH, trifluoromethyl, $CHF_2$, $CH_2F$, $OCHF_2$, trifluoromethylthio, trifluoromethoxy, methylsulfonyl, carboxyl, trifluoromethylsulfonyl, cyano, carbamoyl, sulfamoyl and acetyl; O—P, with P selected from the group consisting of aryl, $C_{8-20}$-alkyl, heteroaryl, C(O)-aryl, C(O)-heteroaryl, and C(O)—$C_{1-20}$-alkyl;

$R^{18}$ represents a hydrogen atom or a branched or linear $C_{1-3}$-alkyl group, while $R^{19}$ represents

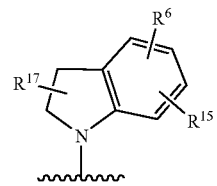

with $R^{15}$, $R^{16}$ and $R^{17}$ are independently from one another selected from the group consisting of H, F, Cl, Br, I, OH, SH, $C_{1-4}$alkyl, $C_{1-4}$alkoxy, $CF_3$, $CHF_2$, $CH_2F$, $OCF_3$, a keto-group, $NO_2$ and $NH_2$;

or $R^{18}$ and $R^{19}$ together with the connecting Nitrogen atom represent

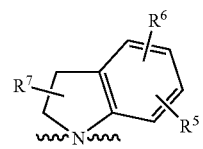

with $R^{15}$, $R^{16}$ and $R^{17}$ are independently from one another selected from the group consisting of H, F, Cl, Br, I, OH, SH, $C_{1-4}$alkyl, $C_{1-4}$alkoxy, $CF_3$, $CHF_2$, $CH_2F$, $OCF_3$, a keto-group, $NO_2$ and $NH_2$;

optionally in the form of a racemic mixture, a purified stereoisomer, or a mixture of stereoisomers;

in the form shown or in the form of an acid or a base or in the form of a salt, or in the form of a corresponding N-oxide thereof.

4. An indoline-substituted pyrazoline compound of general formulas IIa and IIb according to claim 3,

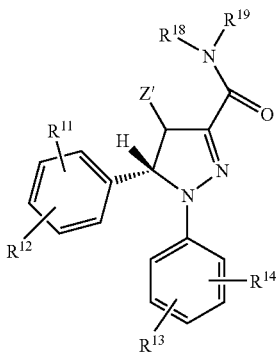

IIa

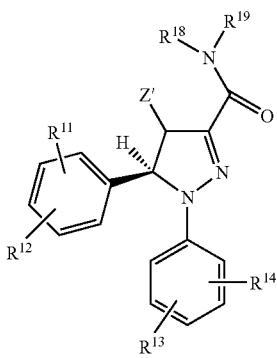

IIb wherein
Z' is $C_{1-4}$-Alkyl, wherein $C_{1-4}$-Alkyl is substituted or unsubstituted, branched or linear, saturated or unsaturated;
$R^{11}$, $R^{12}$, $R^{13}$ and $R^{14}$ are independently of one another selected from the group consisting of:
H; branched or linear $C_{1-3}$-alkyl or branched or linear $C_{1-3}$-alkoxy, phenyl, hydroxy, chloro, bromo, fluoro, iodo, SH, trifluoromethyl, trifluoromethylthio, trifluoromethoxy, $CHF_2$, $CH_2F$, $OCHF_2$, methylsulfonyl, carboxyl, trifluoromethylsulfonyl, cyano, carbamoyl, sulfamoyl and acetyl; O—P, with P selected from the group consisting of aryl, $C_{8-20}$-alkyl, heteroaryl, C(O)-aryl, C(O)-heteroaryl, and C(O)—$C_{1-20}$-alkyl;
$R^{18}$ represents a hydrogen atom or a branched or linear $C_{1-3}$-alkyl group, while $R^{19}$ represents

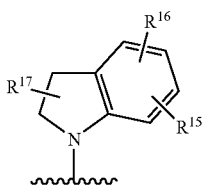

with $R^{15}$, $R^{16}$ and $R^{17}$ are independently from one another selected from the group consisting of H, F, Cl, Br, I, OH, SH, $C_{1-4}$alkyl, $C_{1-4}$ alkoxy, $CF_3$, $CHF_2$, $CH_2F$, $OCF_3$, a keto-group, $NO_2$ and $NH_2$;
or
$R^{18}$ and $R^{19}$ together with the connecting Nitrogen atom represent

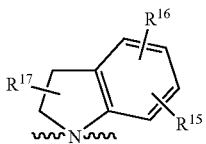

with $R^{15}$, $R^{16}$ and $R^{17}$ are independently from one another selected from the group consisting of H, F, Cl, Br, I, OH, SH, $C_{1-4}$alkyl, $C_{1-4}$alkoxy, $CF_3$, $CHF_2$, $CH_2F$, $OCF_3$, a keto-group, $NO_2$ and $NH_2$;
optionally in the form shown or in the form of an acid or a base or in the form of a salt, or in the form of a corresponding N-oxide thereof.

5. An indoline-substituted pyrazoline compound according to claim 3, characterized in that
$R^{11}$, $R^{12}$, $R^{13}$ and $R^{14}$ are independently of one another selected from the group consisting of H, $CH_3$, $C_2H_5$, $C_3H_7$, $OCH_3$, $OC_2H_5$, OH, SH, F, Cl, Br, I $CF_3$, $CHF_2$, $CH_2F$, $OCF_3$, and $OCHF_2$.

6. An indoline-substituted pyrazoline compound according to claim 3, characterized in that
$R^{18}$ represents H.

7. An indoline-substituted pyrazoline compound according to claim 3, characterized in that
$R^{15}$, $R^{16}$ and $R^{17}$ are independently from one another selected from the group consisting of H, F, Cl, Br, I, OH, $CH_3$, $C_2H_5$, $OCH_3$, $OCF_3$, and $CF_3$.

8. An indoline-substituted pyrazoline compound of general formula III according to claim 1,

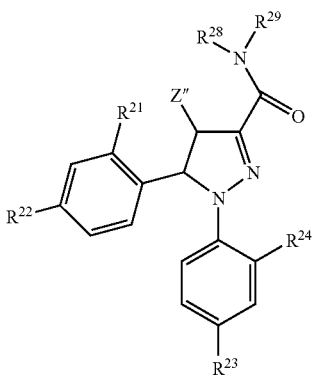

III wherein
Z" is $CH_3$ or $C_2H_5$;
$R^{21}$, $R^{22}$, $R^{23}$ and $R^{24}$ are independently of one another selected from the group consisting of:
H; branched or linear $C_{1-3}$-alkyl or branched or linear $C_{1-3}$-alkoxy, phenyl, hydroxy, chloro, bromo, fluoro, iodo, SH, trifluoromethyl, trifluoromethylthio, trifluoromethoxy, methylsulfonyl, carboxyl, trifluoromethylsulfonyl, cyano, carbamoyl, sulfamoyl and acetyl; O—P, with P selected from the group consisting of aryl, $C_{8-20}$-alkyl, heteroaryl, C(O)-aryl, C(O)-heteroaryl, and C(O)—$C_{1-20}$-alkyl;

$R^{28}$ represents a hydrogen atom or a branched or linear $C_{1-3}$-alkyl group, while $R^{29}$ represents

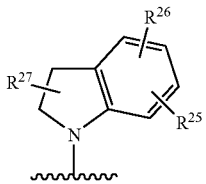

with $R^{25}$, $R^{26}$ and $R^{27}$ are independently from one another selected from the group consisting of H, F, Cl, Br, I, OH, SH, $C_{1-4}$alkyl, $C_{1-4}$alkoxy, $CF_3$, $CHF_2$, $CH_2F$, $OCF_3$, a keto-group, $NO_2$ and $NH_2$;

or $R^{28}$ and $R^{29}$ together with the connecting Nitrogen atom represent

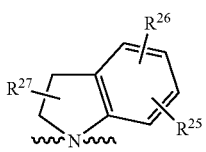

with $R^{25}$, $R^{26}$ and $R^{27}$ are independently from one another selected from the group consisting of H, F, Cl, Br, I, OH, SH, $C_{1-4}$alkyl, $C_{1-4}$alkoxy, $CF_3$, $CHF_2$, $CH_2F$, $OCF_3$, a keto-group, $NO_2$ and $NH_2$;

optionally in the form of a racemic mixture, a purified stereoisomer, or a mixture of stereoisomers;

in the form shown or in the form of an acid or a base or in the form of a salt, or in the form of a corresponding N-oxide thereof.

9. An indoline-substituted pyrazoline compound of general formulas IIIa and IIIb according to claim 8,

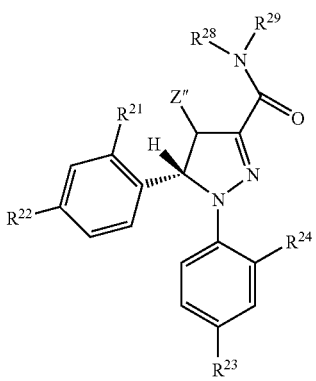

IIIa

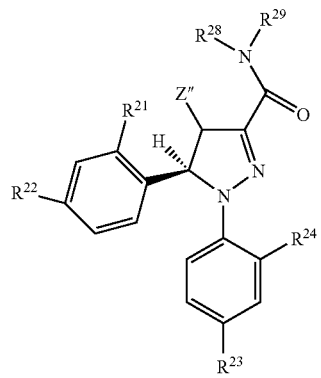

IIIb wherein

Z" is $CH_3$ or $C_2H_5$;

$R^{21}$, $R^{22}$, $R^{23}$ and $R^{24}$ are independently of one another selected from the group consisting of:

H; branched or linear $C_{1-3}$-alkyl or branched or linear $C_{1-3}$-alkoxy, phenyl, hydroxy, chloro, bromo, fluoro, iodo, SH, trifluoromethyl, trifluoromethylthio, trifluoromethoxy, methylsulfonyl, carboxyl, trifluoromethylsulfonyl, cyano, carbamoyl, sulfamoyl and acetyl; O—P, with P selected from the group consisting of aryl, $C_{8-20}$-alkyl, heteroaryl, C(O)-aryl, C(O)-heteroaryl, and C(O)—$C_{1-20}$-alkyl;

$R^{28}$ represents a hydrogen atom or a branched or linear $C_{1-3}$-alkyl group, while $R^{29}$ represents

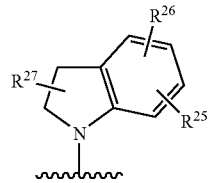

with $R^{25}$, $R^{26}$ and $R^{27}$ are independently from one another selected from the group consisting of H, F, Cl, Br, I, OH, SH, $C_{1-4}$alkyl, $C_{1-4}$alkoxy, $CF_3$, $CHF_2$, $CH_2F$, $OCF_3$, a keto-group, $NO_2$ and $NH_2$;

or $R^{28}$ and $R^{29}$ together with the connecting Nitrogen atom represent

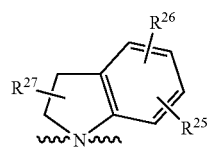

with $R^{25}$, $R^{26}$ and $R^{27}$ are independently from one another selected from the group consisting of H, F, Cl, Br, I, OH, SH, $C_{1-4}$alkoxy, $CF_3$, $CHF_2$, $CH_2F$, $OCF_3$, a keto-group, $NO_2$ and $NH_2$;

optionally in the form shown or in the form of an acid or a base or in the form of a salt, or in the form of a corresponding N-oxide thereof.

10. An indoline-substituted pyrazoline compound according to claim 8, characterized in that $R^{21}$ represents; O—P, with P selected from the group consisting of aryl, $C_{8-20}$-alkyl, heteroaryl, C(O)-aryl, C(O)-heteroaryl, and C(O)—$C_{1-20}$-alkyl, while $R^{22}$, $R^{23}$ and $R^{24}$ are independently of one another selected from the group consisting of H, $CH_3$, $C_2H_5$, $C_3H_7$, $OCH_3$, $OC_2H_5$, OH, SH, F, Cl, Br, I $CF_3$, $CHF_2$, $CH_2F$, $OCF_3$, and $OCHF_2$.

11. An indoline-substituted pyrazoline compound according to claim 8, characterized in that
$R^{21}$, $R^{22}$, $R^{23}$ and $R^{24}$ are independently of one another selected from the group consisting of H, $CH_3$, $C_2H_5$, $C_3H_7$, $OCH_3$, $OC_2H_5$, OH, SH, F, Cl, Br, I $CF_3$, $CHF_2$, $CH_2F$, $OCF_3$, and $OCHF_2$.

12. An indoline-substituted pyrazoline compound according to claim 8, characterized in that
$R^{28}$ represents H.

13. Process for the manufacture of an indoline-substituted pyrazoline compound of general formula I according to claim 1, characterized in that at least one benzaldehyde compound of general formula V

(V)

wherein X has the meaning according to claim 1, is reacted with a pyruvate compound of general formula (VI)

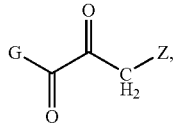
(VI)

wherein Z has the meaning according to claim 1; and G represents an OR group with R being H or a branched or unbranched $C_{1-6}$ alkyl radical or G represents an O—K group with K being a cation,
to yield a compound of general formula (VII)

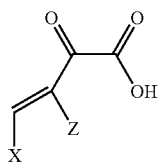
(VII)

wherein X and Z have the meaning given above, which is optionally isolated and/or optionally purified, and which is reacted with an optionally substituted phenyl hydrazine of general formula (VIII)

(VIII)

or a corresponding salt thereof, wherein Y has the meaning according to claim 1, under inert atmosphere, to yield a compound of general formula (IX)

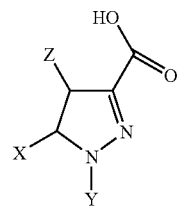
(IX)

wherein X, Z and Y have the meaning as given above, which is optionally isolated and/or optionally purified, and optionally transferred under inert atmosphere to a compound of general formula (XI) via the reaction with an activating agent

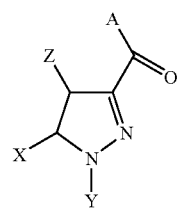
(XI)

wherein the substituents X, Z and Y have the meaning given above and A represents a leaving group, said compound being optionally isolated and/or optionally purified, and at least one compound of general formula (XI) is reacted with a compound of general formula XII or XIIa

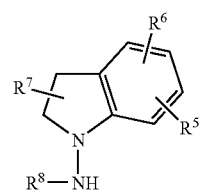
(XII)

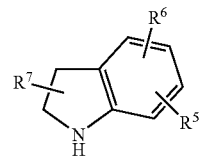
(XIIa)

Wherein $R^5$, $R^6$, $R^7$ and $R^8$ are defined as in claim 1; under inert atmosphere to yield a substituted pyrazoline compound of general formula I, which is optionally isolated and/or optionally purified.

14. Medicament comprising at least one substituted pyrazoline compound of general formula I according to claim 1, and optionally one or more pharmaceutically acceptable excipients.

15. A method for the treatment of obesity, the method comprising administering to a patient a compound of claim 1 and optionally one or more pharmaceutically acceptable excipients.

16. An indoline-substituted pyrazoline compound according to claim 3, wherein
Z' is $CH_3$ or $C_2H_5$.

17. An indoline-substituted pyrazoline compound according to claim 4, wherein
Z' is $CH_3$ or $C_2H_5$.

18. An indoline-substituted pyrazoline compound according to claim 5, wherein
$R^{11}$, $R^{12}$, $R^{13}$ and $R^{14}$ are independently of one another selected from the group consisting of H, OH, $OCH_3$, F, Cl, Br, I, $CF_3$, $CHF_2$ and $OCF_3$.

19. An indoline-substituted pyrazoline compound according to claim 10, wherein
$R^{21}$ represents O—P, wherein P is selected from the group consisting of aryl, $C_{8-20}$-alkyl, heteroaryl, C(O)-aryl, C(O)-heteroaryl, and C(O)—$C_{1-20}$-alkyl, while $R^{22}$, $R^{23}$ and $R^{24}$ are independently of one another selected from the group consisting of H, OH, $OCH_3$, F, Cl, Br, I, $CF_3$, $CHF_2$ and $OCF_3$.

20. An indoline-substituted pyrazoline compound according to claim 19, wherein
$R^{21}$ represents O—P, wherein P is selected from the group consisting of aryl, $C_{8-20}$-alkyl, heteroaryl, C(O)-aryl, C(O)-heteroaryl, and C(O)—$C_{1-20}$-alkyl, while $R^{22}$, $R^{23}$ and $R^{24}$ are independently of one another selected from the group consisting of OH, $OCH_3$, F, Cl, Br, I and $OCF_3$.

21. An indoline-substituted pyrazoline compound according to claim 11, wherein
$R^{21}$, $R^{22}$, $R^{23}$ and $R^{24}$ are independently of one another selected from the group consisting of H, OH, $OCH_3$, F, Cl, Br, I, $CF_3$, $CHF_2$ and $OCF_3$.

22. An indoline-substituted pyrazoline compound according to claim 21, wherein
$R^{21}$ represents H, while $R^{22}$, $R^{23}$ and $R^{24}$ are independently of one another selected from the group consisting of OH, $OCH_3$, F, Cl, Br, I and $OCF_3$.

* * * * *